United States Patent
Hiyoshi et al.

(10) Patent No.: US 8,455,413 B2
(45) Date of Patent: Jun. 4, 2013

(54) ADDITIVE FOR OILS AND LUBRICANT COMPRISING THE SAME

(75) Inventors: Satoshi Hiyoshi, Yokkaichi (JP); Shingo Nakayama, Yokkaichi (JP); Nobuhito Amemiya, Mie-gun (JP); Shigeaki Kato, Yokkaichi (JP); Toshihiro Inayama, Yokkaichi (JP); Yukihiro Isogai, Nagoya (JP); Ichiro Minami, Morioka (JP); Shigeyuki Mori, Morioka (JP)

(73) Assignee: KH Neochem Co., Ltd., Tokyo (JP)

( * ) Notice: Subject to any disclaimer, the term of this patent is extended or adjusted under 35 U.S.C. 154(b) by 507 days.

(21) Appl. No.: 12/598,953

(22) PCT Filed: May 7, 2008

(86) PCT No.: PCT/JP2008/058465
§ 371 (c)(1),
(2), (4) Date: May 26, 2010

(87) PCT Pub. No.: WO2008/139992
PCT Pub. Date: Nov. 20, 2008

(65) Prior Publication Data
US 2010/0298183 A1    Nov. 25, 2010

(30) Foreign Application Priority Data
May 8, 2007    (JP) .................... P2007-123389

(51) Int. Cl.
*C10M 105/32* (2006.01)
*C10M 105/68* (2006.01)
*C10M 145/22* (2006.01)

(52) U.S. Cl.
USPC ........... 508/476; 508/459; 508/463; 508/465; 508/500; 508/506; 508/508; 508/513

(58) Field of Classification Search
USPC ............... 508/459, 463, 464, 465, 476, 500, 508/506, 508, 513
See application file for complete search history.

(56) References Cited

U.S. PATENT DOCUMENTS 5,190,999 A * 3/1993 Nesvadba ................. 524/96

FOREIGN PATENT DOCUMENTS

| | | |
|---|---|---|
| GB | 802 727 | 10/1958 |
| JP | 46-37338 | 11/1971 |
| JP | 50-106881 | 8/1975 |
| JP | 61-167436 | 7/1986 |
| JP | 62-039696 | 2/1987 |
| JP | 62-125079 | 6/1987 |
| JP | 1-501319 | 5/1989 |
| JP | 4-244051 | 9/1992 |
| JP | 2563295 | 9/1996 |
| JP | 2004-262964 | 9/2004 |
| JP | 2005-048192 | 2/2005 |
| JP | 2005-263747 | 9/2005 |
| WO | 86/04601 | 8/1986 |
| WO | 88/03552 | 5/1988 |
| WO | 2005/003088 | 1/2005 |

* cited by examiner

*Primary Examiner* — Taiwo Oladapo
(74) *Attorney, Agent, or Firm* — Fitzpatrick, Cella, Harper & Scinto

(57) ABSTRACT

An additive for oils that is capable of imparting oils such as lubricant base oils with superior wear resistance properties or friction resistance properties, and a lubricant. An additive for oils that includes a compound represented by formula (I) is used. A and B each represents a single bond or hydrocarbylene or the like, X and Y each represents a sulfur atom or single bond, and W and Z each represents a hydrogen atom or $-NR^1R^2$ or the like, provided that W and Z are not both hydrogen atoms. $R^1$ and $R^2$ each represents a hydrogen atom, a hydrocarbyl or a hydrocarbylcarbonyl or the like, and n and m each represents an integer of 0 to 5.

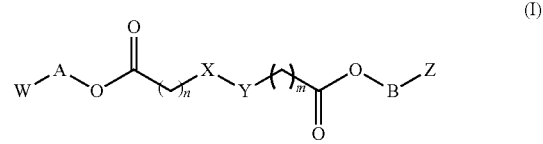

(I)

9 Claims, No Drawings

ADDITIVE FOR OILS AND LUBRICANT COMPRISING THE SAME

Priority is claimed on Japanese Patent Application No. 2007-123389, filed May 8, 2007, the content of which is incorporated herein by reference.

BACKGROUND OF THE INVENTION

1. Field of the Invention

The present invention relates to an additive for oils that imparts wear resistance properties or friction resistance properties to oils such as lubricant base oils or fuel oils.

2. Description of the Related Art

In recent years, the rapid growth of industry and the increase in market penetration of automobiles and electrical appliances in China, India and Southeast Asia, or the like, have resulted in a dramatic increase in worldwide energy demands. At the same time, environmental impact concerns are beginning to grow worldwide, and all manner of regulations relating to energy conservation, typified by the Kyoto Protocol, are being introduced to alleviate environmental problems such as global warming and acid rain caused by exhaust gases, and the destruction of the ozone layer.

As part of this environmental movement, there are increasingly strong demands for lubricants, and particularly automobile engine oils, that provide lower fuel consumption and longer drain times. At the same time, upper limits have been set for the concentration levels of the metal fraction, phosphorus fraction and sulfur fraction contained within such lubricants (see Non-Patent Documents 1 and 2). Accordingly, lubricants that contain none of these components, and particularly no metal fraction or phosphorus fraction, are now being demanded.

Lubricants are typically produced by adding additives to a lubricant base oil. It is claimed that selecting a lubricant base oil having a low viscosity and superior heat resistance is effective in improving the fuel consumption provided by the lubricant, and known examples of such lubricant base oils include polar base oils such as esters (see Patent Document 1).

Further, lubricants also require all manner of other properties, including wear resistance and friction resistance. Accordingly, as disclosed in Patent Documents 2 to 5, various additives capable of imparting lubricants with wear resistance and friction resistance have been investigated.

[Patent Document 1]
Japanese Laid-Open Patent Application No. 2005-48192
[Patent Document 2]
Japanese Examined Patent Application, Second Publication No. Hei 6-4867
[Patent Document 3]
Japanese Patent (Granted) Publication No. 2,563,295
[Patent Document 4]
Published Japanese translation No. Hei 1-501319 of PCT
[Patent Document 5]
Japanese Laid-Open Patent Application No. 2004-262964
[Non-Patent Document 1] "Journal of Economic Maintenance Tribology", July 2005 edition, page 7
[Non-Patent Document 2] "Monthly Tribology", December 2005 edition, page 36

SUMMARY OF THE INVENTION

Maintaining pace with the rapidly improving environmental performance of automobiles requires a combination of increased output and smaller and lighter vehicles, meaning increasingly high levels of thermal stability are now being demanded of the lubricants used in these vehicles. Particularly in the case of automobile transmission oils, the stable retention of a uniform coefficient of friction, even under conditions of extreme heat and pressure, is required to suppress any undesirable shudder or vibration from being conveyed to the driver.

An object of the present invention is to provide an additive for oils containing an ester that is capable of imparting oils such as lubricant base oils with superior wear resistance properties or friction resistance properties, as well as a lubricant that contains such an additive for oils.

As a result of intensive investigation, the inventors of the present invention discovered that by using an ester having an introduced nitrogen atom as an additive for oils, the object described above could be achieved, and they were therefore able to complete the present invention. In other words, the present invention provides the aspects (1) to (17) described below.

(1) An additive for oils, including an ester represented by formula (I):

[Chemical Formula 1]

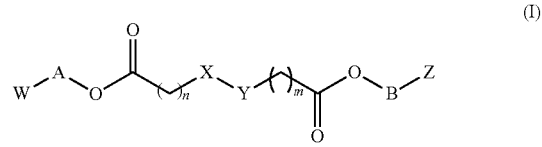

wherein A and B are identical or different and each represents a single bond or a hydrocarbylene, n and m are identical or different and each represents an integer of 0 to 5, X and Y are identical or different and each represents a sulfur atom or a single bond, and W and Z are identical or different and each represents a hydrogen atom, a group represented by formula (II):

[Chemical Formula 2]

$$-NR^1R^2 \qquad (II)$$

wherein $R^1$ and $R^2$ are identical or different, and either each represents a hydrogen atom, a hydrocarbyl that optionally has one or more substituents, a hydrocarbylcarbonyl that optionally has one or more substituents or a hydrocarbyloxycarbonyl that optionally has one or more substituents, or $R^1$ and $R^2$ form a nitrogen-containing heterocyclic group that optionally has one or more substituents in combination with the adjacent nitrogen atom, or a group represented by formula (III):

[Chemical Formula 3]

$$-N=CR^3R^4 \qquad (III)$$

wherein $R^3$ and $R^4$ are identical or different, and either each represents a hydrogen atom or a hydrocarbyl that optionally has one or more substituents, or $R^3$ and $R^4$ form a cyclic hydrocarbylidene that optionally has one or more substituents in combination with the adjacent carbon atom, provided that W and Z do not both represent hydrogen atoms.

(2) The additive for oils according to (1) above, wherein at least one of X and Y represents a sulfur atom.

(3) The additive for oils according to (1) above, wherein X and Y are the same, and both represent sulfur atoms.

(4) The additive for oils according to (1) above, wherein X and Y both represent single bonds.

(5) The additive for oils according to any one of (1) to (4) above, wherein the sum of n and m represents an integer of 2 to 10.
(6) The additive for oils according to any one of (1) to (4) above, wherein the sum of n and m represents an integer of 4 to 8.
(7) The additive for oils according to any one of (1) to (6) above, wherein A and B are identical or different and each represents a single bond, an alkylene, an alkenylene, a cycloalkylene that optionally has one or more substituents, or an arylene that optionally has one or more substituents.
(8) The additive for oils according to any one of (1) to (6) above, wherein A and B are identical, and both represent an alkylene or an arylene that optionally has one or more substituents.
(9) The additive for oils according to any one of (1) to (6) above, wherein A and B are identical, and both represent an alkylene of 1 to 20 carbon atoms or an arylene of 6 to 20 carbon atoms that optionally has one or more substituents.
(10) The additive for oils according to any one of (1) to (9) above, wherein W and/or Z is represented by formula (II), and $R^1$ and $R^2$ are identical or different and each represents a hydrogen atom, an alkyl of 1 to 20 carbon atoms that optionally has one or more substituents, an alkenyl of 2 to 20 carbon atoms that optionally has one or more substituents, a cycloalkyl of 3 to 20 carbon atoms that optionally has one or more substituents, an aryl of 6 to 20 carbon atoms that optionally has one or more substituents, an aralkyl of 7 to 20 carbon atoms that optionally has one or more substituents, an alkanoyl of 2 to 21 carbon atoms that optionally has one or more substituents, an alkenoyl of 3 to 21 carbon atoms that optionally has one or more substituents, an alkoxycarbonyl of 2 to 21 carbon atoms that optionally has one or more substituents, or a cycloalkylcarbonyl of 4 to 21 carbon atoms that optionally has one or more substituents.
(11) The additive for oils according to any one of (1) to (9) above, wherein W and/or Z is represented by formula (II), and $R^1$ and $R^2$ are identical or different and each represents a hydrogen atom, an alkyl of 1 to 20 carbon atoms, or an alkanoyl of 2 to 21 carbon atoms.
(12) The additive for oils according to any one of (1) to (9) above, wherein W and/or Z is represented by formula (II), and formula (II) represents a group represented by formula (IV):

[Chemical Formula 4]

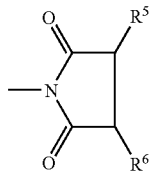

(IV)

wherein $R^5$ and $R^6$ are identical or different, and either each represents a hydrogen atom, an alkyl of 1 to 20 carbon atoms that optionally has one or more substituents, or an alkenyl of 2 to 20 carbon atoms that optionally has one or more substituents, or $R^5$ and $R^6$ form, in combination with the two carbon atoms adjacent thereto, a benzene ring that have optionally an alkyl substituent of 1 to 20 carbon atoms, or a naphthalene ring that have optionally an alkyl substituent of 1 to 20 carbon atoms.
(13) The additive for oils according to (12) above, wherein in formula (IV), one of $R^5$ and $R^6$ represents an octadecyl or octadecenyl group, and the other represents a hydrogen atom.
(14) The additive for oils according to (13) above, wherein in formula (I), m and n both represent 2, and A and B are the same and both represent an ethylene or hexylene group.
(15) An ester compound, wherein in formula (I), m and n both represent 2, A and B are the same and both represent an ethylene, W and Z are both represented by formula (II), and formula (II) is represented by formula (IV), in which one of $R^5$ and $R^6$ represents an octadecyl or octadecenyl group, and the other represents a hydrogen atom.
(16) A lubricant, comprising to additive for oils according to any one of (1) to (14) above, and a lubricant base oil.
(17) The lubricant according to (16) above, wherein the lubricant base oil is a mineral oil, poly-α-olefin, fatty acid ester, polyalkylene glycol, phosphate ester, silicone, silicate ester, polyphenyl ether, alkylbenzene, synthetic naphthene, gas-to-liquid (GTL), or a vegetable oil.

The present invention is able to provide an additive for oils containing an ester that is capable of imparting superior wear resistance properties or friction resistance properties to oils such as lubricant base oils, as well as a lubricant that contains such an additive for oils.

DETAILED DESCRIPTION OF THE INVENTION

The additive for oils of to the present invention is added, for example, to an oil such as a lubricant base oil or a fuel oil or the like, thereby imparting the oil with wear resistance properties or friction resistance properties, and includes an ester represented by formula (I). In the following description, this ester may be referred to as "ester (I)".

Further, in the present invention, a "hydrocarbylene" refers to a divalent group generated by removing two hydrogen atoms from the same carbon atom or different carbon atoms of a hydrocarbon, wherein the group may be saturated or unsaturated, may be linear, branched, cyclic, or a group having a cyclic structure, and is preferably a group of 1 to 30 carbon atoms. A group of 1 to 20 carbon atoms is more preferred. Furthermore, two or more of such groups may be combined. More specific examples of the hydrocarbylene include alkylene, alkenylene, alkynylene, cycloalkylene, cycloalkenylene, arylene or the like.

The linear hydrocarbylene is preferably a group of 1 to 20 carbon atoms. Examples of preferred groups include methylene, ethylene, propylene, butylene, pentylene, hexylene, heptylene, vinylene, propenylene, butenylene, pentenylene, hexenylene, ethynylene, propynylene, butynylene, pentynylene, hexynylene or the like. The branched hydrocarbylene is preferably a group of 3 to 20 carbon atoms. Examples of preferred groups include 1,2-propylene, 1,2-butylene, 1,3-butylene, 2,3-butylene, 1,2-pentylene, 1,3-pentylene, 1,4-pentylene, 2,3-pentylene, 2,4-pentylene, 1,2-hexylene, 1,3-hexylene, 1,4-hexylene, 1,5-hexylene, 2,3-hexylene, 2,4-hexylene, 2,5-hexylene, 3,4-hexylene or the like.

The cyclic hydrocarbylene is preferably a group of 3 to 20 carbon atoms. Preferred groups include cyclopropylene, cyclobutylene, cyclopentylene, cyclohexylene, cycloheptylene, cyclooctylene, cyclododecylene, cyclopropenylene, cyclobutenylene, cyclopentenylene, cyclohexenylene, phenylene, biphenylene, triphenylene, naphthylene, anthracenylene or the like.

Examples of the hydrocarbylene group having a cyclic structure include divalent groups in which an alkylene or alkenylene is bonded to one or both of the bonds from a cyclic hydrocarbylene group, and groups of 4 to 20 carbon atoms are preferred. Preferred examples include benzylene, xylylene or the like.

A "cyclic hydrocarbylidene" refers to a divalent group generated by removing two hydrogen atoms from the same carbon atom of an alicyclic hydrocarbon. Cyclic hydrocarbylidene groups of 3 to 20 carbon atoms are preferred, and specific examples include a cyclopentylidene, cyclohexylidene, cycloheptylidene, 2-cyclopenten-1-ylidene, 2,4-cyclohexadien-1-ylidene, 1,2,3,4-tetrahydro-1-naphthylidene or the like.

An "alkylene" is a divalent group generated by removing two hydrogen atoms from the same carbon atom or different carbon atoms of an alkane, and includes linear and branched groups of 1 to 20 carbon atoms. Preferred examples include methylene, ethylene, propylene, butylene, isobutylene, pentylene, hexylene, heptylene, octylene, nonylene, decylene, undecylene, dodecylene, tridecylene, pentadecylene, eicosylene or the like.

An "alkenylene" is a divalent group generated by removing two hydrogen atoms from the same carbon atom or different carbon atoms of an alkene, and includes linear and branched groups of 2 to 20 carbon atoms. Preferred examples include vinylene, propenylene, butenylene, pentenylene, hexenylene, decenylene, undecenylene, pentadecenylene, eicosenylene or the like.

An "alkynylene" is a divalent group generated by removing two hydrogen atoms from the same carbon atom or different carbon atoms of an alkyne, and includes linear and branched groups of 2 to 20 carbon atoms. Preferred examples include ethynylene, propargylene (propynylene), butynylene, pentynylene, hexynylene, decynylene, pentadecynylene, eicosynylene or the like.

A "cycloalkylene" is a divalent group generated by removing two hydrogen atoms from the same carbon atom or different carbon atoms of a cycloalkane, and is preferably a group of 3 to 20 carbon atoms. Preferred examples include cyclopropylene, cyclobutylene, cyclopentylene, cyclohexylene, cyclodecylene, cyclopentadecylene, cycloeicosylene or the like.

A "cycloalkenylene" is a divalent group generated by removing two hydrogen atoms from the same carbon atom or different carbon atoms of a cycloalkene, and is preferably a group of 3 to 20 carbon atoms. Preferred examples include cyclopropenylene, cyclobutenylene, cyclopentenylene, cyclohexenylene, cyclodecenylene, cyclopentadecenylene, cycloeicosenylene or the like.

An "arylene" is a divalent group generated by removing one hydrogen atom from each of two different carbon atoms of an aromatic hydrocarbon, and is preferably a group of 6 to 20 carbon atoms. Preferred examples include phenylene, tolylene, naphthylene, biphenylene, anthracenylene, naphthacenylene, pyrenylene or the like.

Further, in the description of the present invention, a "hydrocarbyl" is a monovalent group generated by removing a single hydrogen atom from a hydrocarbon, wherein the group optionally has one or more substituents, may be saturated or unsaturated, and may be linear, branched, cyclic, or a group having a cyclic structure. The hydrocarbyl is preferably a group of 1 to 30 carbon atoms, and more preferably 1 to 20 carbon atoms. More specific preferable examples of the hydrocarbyl include alkyl, alkenyl, alkynyl, cycloalkyl, cyclolalkenyl, aralkyl and aryl or the like.

Examples of the saturated hydrocarbyl groups include alkyl, cycloalkyl or the like.

Examples of the unsaturated hydrocarbyl groups include alkenyl, alkynyl, aryl, cycloalkenyl, aralkyl or the like.

Examples of the linear hydrocarbyl groups include linear alkyl, linear alkenyl, and linear alkynyl or the like, and groups of 1 to 20 carbon atoms are preferred.

Examples of the branched hydrocarbyl groups include branched alkyl, branched alkenyl and branched alkynyl or the like.

Examples of the cyclic hydrocarbyl groups include cycloalkyl, cycloalkenyl and aryl or the like.

Examples of the hydrocarbyl groups having a cyclic structure include groups in which a hydrogen atom of an alkyl or alkenyl group is substituted with a cyclic hydrocarbyl group, and groups of 4 to 20 carbon atoms are preferred. Specific examples include benzyl, biphenylmethyl, naphthylmethyl, 2-phenylvinyl-1-yl or the like.

In a hydrocarbylcarbonyl, the hydrocarbyl portion is as defined above for the hydrocarbyl groups.

The hydrocarbylcarbonyl is preferably a group of 2 to 21 carbon atoms, and examples include alkanoyl, alkenoyl, cycloalkylcarbonyl, aroyl or the like In a hydrocarbyloxycarbonyl, the hydrocarbyl portion is as defined above for the hydrocarbyl groups.

The hydrocarbyloxycarbonyl is preferably a group of 2 to 21 carbon atoms, and examples include alkoxycarbonyl, cycloalkyloxycarbonyl, alkenyloxycarbonyl, aryloxycarbonyl, aralkyloxycarbonyl or the like.

Examples of the alkyl groups include linear or branched alkyl groups of 1 to 20 carbon atoms or the like. Specific examples of the linear alkyl groups of 1 to 20 carbon atoms include methyl, ethyl, propyl, butyl, pentyl, hexyl, heptyl, octyl, nonyl, decyl, undecyl, dodecyl, tridecyl, tetradecyl, hexadecyl, octadecyl or the like. A hexyl or the like is particularly preferred. Specific examples of the branched alkyl groups of 3 to 20 carbon atoms include isobutyl, sec-butyl, tert-butyl, neopentyl or the like.

Examples of the alkenyl groups include linear or branched alkenyl groups of 2 to 20 carbon atoms or the like. Specific examples of the linear alkenyl groups of 2 to 20 carbon atoms include vinyl, allyl, 3-buten-1-yl, 2-buten-1-yl, 1-buten-1-yl, 4-penten-1-yl, 3-penten-1-yl, 2-penten-1-yl, 1-penten-1-yl, octadecenyl, octadecadienyl or the like. An octadecenyl, oleyl or the like is preferred, and an oleyl or the like is particularly desirable. Specific examples of the branched alkenyl groups of 3 to 20 carbon atoms include isopropenyl, 2-methyl-1-propen-1-yl groups or the like.

Examples of the alkynyl groups include linear or branched alkynyl groups of 2 to 20 carbon atoms. Specific examples of the linear alkynyl groups of 2 to 20 carbon atoms include ethynyl, propargyl (propynyl), butynyl, pentynyl, hexynyl, heptynyl, octynyl, nonyl, decynyl, undecynyl, dodecynyl, tridecynyl, tetradecynyl, hexadecynyl, octadecynyl or the like. A specific example of the branched alkynyl groups of 4 to 20 carbon atoms is a 3-methyl-1-butyn-1-yl group.

As the cycloalkane, compounds of 3 to 20 carbon atoms are preferred, and specific examples include cyclopropane, cyclobutane, cyclopentane, cyclohexane, cycloheptane, cyclooctane, cyclononane, cyclodecane, cyclopentadecane, cycloeicosane or the like.

The cycloalkyl is preferably a group of 3 to 20 carbon atoms, and specific examples include cyclopropyl, cyclobutyl, cyclopentyl, cyclohexyl, cycloheptyl, cyclooctyl, cyclononyl, cyclodecyl, cyclopentadecyl, cycloeicosyl or the like.

The cycloalkenyl is preferably a group of 3 to 20 carbon atoms, and specific examples include cyclopropenyl, cyclobutenyl, cyclopentenyl, cyclohexenyl, cycloheptenyl, cyclooctenyl, cyclononeyl, cyclodecenyl, cyclopentadecenyl, cycloeicosenyl or the like.

In an alkanoyl, the alkyl portion is as defined above for the alkyl groups.

The alkanoyl is preferably a group of 2 to 21 carbon atoms, and specific examples include acetyl, propionyl, pivaloyl, propioloyl, butyloyl, pentyloyl, hexyloyl, heptyloyl, octyloyl, nonanoyl, decanoyl, dodecanoyl, tridecanoyl, tetradecanoyl, hexadecanoyl, octadecanoyl or the like. An acetyl or the like is particularly desirable.

In an alkenoyl, the alkenyl portion is as defined above for the alkenyl groups.

The alkenoyl is preferably a group of 3 to 21 carbon atoms, and specific examples include acryloyl, methacryloyl, octadecenoyl, octadecadienoyl, oleoyl or the like. Of these, an octadecenoyl, oleoyl or the like is preferred, and an oleoyl or the like is particularly desirable.

The aryl is preferably a group of 6 to 20 carbon atoms, and specific examples include phenyl, biphenyl, triphenyl, naphthyl, pyranyl or the like.

In an aralkyl, the alkyl portion is as defined above for the alkyl, and the aryl portion is as defined above for the aryl.

The aralkyl is preferably a group of 7 to 20 carbon atoms, and specific examples include benzyl, phenethyl, 3-phenylpropyl, naphthylmethyl, biphenylmethyl or the like.

In an aroyl, the aryl portion is as defined above for the aryl.

The aroyl is preferably a group of 7 to 21 carbon atoms, and specific examples include a benzoyl, naphthoyl, toluoyl, xyloyl or the like.

In a cycloalkylcarbonyl, the cycloalkyl portion is as defined above for the cycloalkyl.

The cycloalkylcarbonyl is preferably a group of 4 to 21 carbon atoms, and specific examples include cyclopropylcarbonyl, cyclobutylcarbonyl, cyclopentylcarbonyl, cyclohexylcarbonyl or the like.

In an alkoxycarbonyl, the alkyl portion is as defined above for the alkyl groups.

The alkoxycarbonyl is preferably a group of 2 to 21 carbon atoms, and specific examples include methoxycarbonyl, ethoxycarbonyl, propyloxycarbonyl, tert-butoxycarbonyl (BOC) or the like.

In a cycloalkyloxycarbonyl, the cycloalkyl portion is as defined above for the cycloalkyl groups.

The cycloalkyloxycarbonyl is preferably a group of 4 to 21 carbon atoms, and specific examples include cyclopropyloxycarbonyl, cyclopentyloxycarbonyl, cyclohexyloxycarbonyl or the like.

In an alkenyloxycarbonyl, the alkenyl portion is as defined above for the alkenyl.

The alkenyloxycarbonyl is preferably a group of 3 to 21 carbon atoms, and a specific example is an allyloxycarbonyl or the like.

In an aryloxycarbonyl, the aryl portion is as defined above for the aryl.

The aryloxycarbonyl is preferably a group of 7 to 21 carbon atoms, and more preferred examples include phenyloxycarbonyl, naphthyloxycarbonyl, biphenyloxycarbonyl or the like.

In an aralkyloxycarbonyl, the aralkyl portion is as defined above for the aralkyl groups.

The aralkyloxycarbonyl is preferably a group of 8 to 21 carbon atoms, and specific examples include benzyloxycarbonyl, naphthylmethyloxycarbonyl or the like.

As the aromatic hydrocarbon, compounds of 6 to 20 carbon atoms are preferred, and preferred examples include benzene, toluene, naphthalene, biphenyl, anthracene, naphthacene, pyrene or the like.

Examples of the nitrogen-containing heterocyclic group include 5-membered or 6-membered monocyclic heterocyclic groups which, besides one nitrogen atom, may also include an atom selected from among a nitrogen atom, an oxygen atom and a sulfur atom, and condensed bicyclic or tricyclic heterocyclic groups containing condensed 3- to 8-membered rings, which, besides one nitrogen atom, may also include an atom selected from among a nitrogen atom, an oxygen atom and a sulfur atom. Specific examples include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxazolidinyl, morpholino, thiazolidinyl, thiomorpholino, 2H-oxazolyl, 2H-thiazolyl, dihydroindolyl, dihydroisoindolyl, dihydrobenzisoindolyl, benzimidazolidinyl, dihydrobenzoxazolyl, dihydrobenzothiazolyl, tetrahydroquinolyl, tetrahydroisoquinolyl, tetrahydroquinoxalinyl, tetrahydroquinazolinyl, 2-pyrrolidinon-1-yl, 2-piperidinon-1-yl or the like.

The substituent of the alkanoyl that optionally has one or more substituents, the substituent of the alkenoyl that optionally has one or more substituents, the substituent of the hydrocarbyl that optionally has one or more substituents, the substituent of the hydrocarbylcarbonyl that optionally has one or more substituents, the substituent of the hydrocarbyloxycarbonyl that optionally has one or more substituents, the substituent of the alkyl that optionally has one or more substituents, the substituent of the alkenyl that optionally has one or more substituents, the substituent of the aralkyl that optionally has one or more substituents, the substituent of the alkoxycarbonyl that optionally has one or more substituents, and the substituent of the cycloalkylcarbonyl that optionally has one or more substituents each represents 1 to 5 substituents that may be the same or different, wherein specific examples of the substituent include hydroxyl, formyl, epoxy, carboxyl, mercapto, amino, hydrazino, imino, azo, nitro, cyano, oxime, alkoxy, alkylthio, alkyldithio or the like.

The alkyl portion within these alkoxy, alkylthio and alkyldithio substituents is as defined above for the alkyl.

The substituent of the aryl that optionally has one or more substituents, the substituent of the cycloalkyl that optionally has one or more substituents, the substituent of the benzene ring that optionally has one or more substituents, the substituent of the naphthalene ring that optionally has one or more substituents, and the substituent of the cyclic hydrocarbylidene that optionally has one or more substituents, each represents 1 to 5 substituents that may be the same or different, wherein specific examples of the substituent include alkyl, alkoxy, alkylthio, alkyldithio, alkenyl, alkynyl, hydroxyl, formyl, epoxy, carboxyl, mercapto, amino, hydrazino, imino, azo, nitro, cyano, oxime or the like.

These alkyl, alkenyl and alkynyl are as defined above.

The alkyl portion within the alkoxy, alkylthio and alkyldithio substituents is as defined above for the alkyl.

The substituent of the nitrogen-containing heterocyclic group that optionally has one or more substituents represents 1 to 5 substituents that may be the same or different, wherein specific examples of the substituent include alkyl, alkenyl, alkynyl, oxo, hydroxyl, formyl, epoxy, carboxyl, mercapto, amino, hydrazino, imino, azo, nitro, cyano, oxime or the like.

These alkyl, alkenyl and alkynyl groups are as defined above.

The number of substituents within the benzene ring that have optionally an alkyl substituent of 1 to 20 carbon atoms is preferably 0 to 2.

The number of substituents within the naphthalene ring that have optionally an alkyl substituent of 1 to 20 carbon atoms is preferably 0 to 5.

The substituent of the arylene that optionally has one or more substituents and the substituent of the cycloalkylene that optionally has one or more substituents each represents 1 to 4 substituents that may be the same or different, wherein specific examples of the substituent include alkyl, alkenyl, alkynyl or the like.

These alkyl, alkenyl and alkynyl are as defined above.

Specific examples of the ester used in the present invention include ester (I-1) to ester (I-12) shown below or the like.

[Chemical Formula 5]

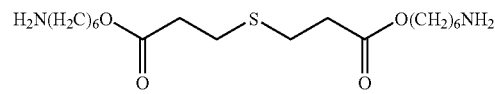
(I-1)

[Chemical Formula 6]

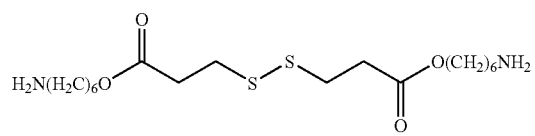
(I-2)

[Chemical Formula 7]

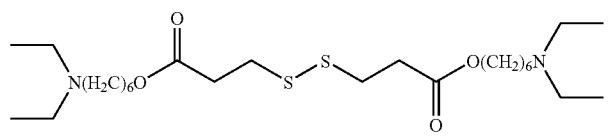
(I-3)

[Chemical Formula 8]

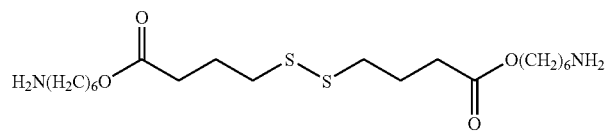
(I-4)

[Chemical Formula 9]

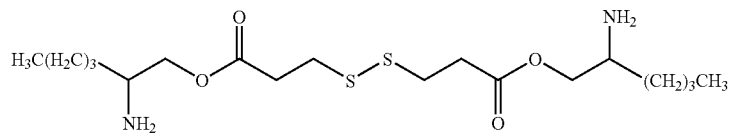
(I-5)

[Chemical Formula 10]

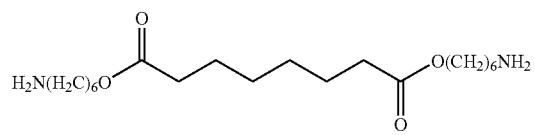
(I-6)

[Chemical Formula 11]

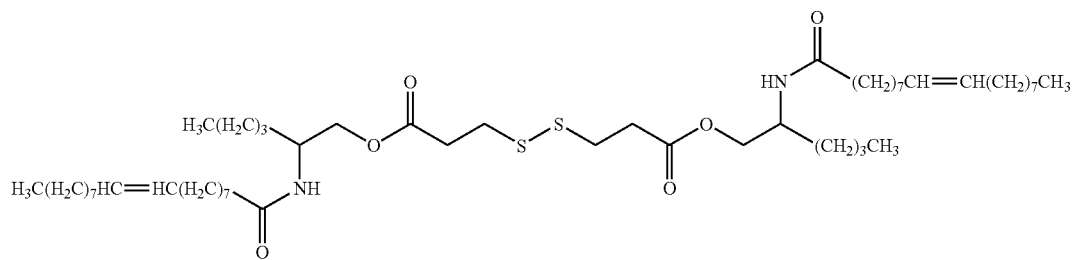
(I-7)

-continued

[Chemical Formula 12]

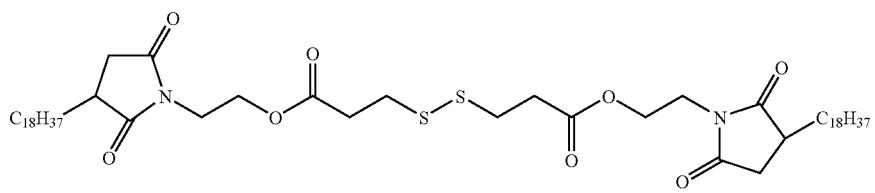

(I-8)

[Chemical Formula 13]

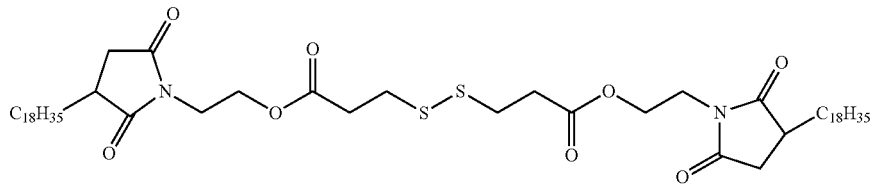

(I-9)

[Chemical Formula 14]

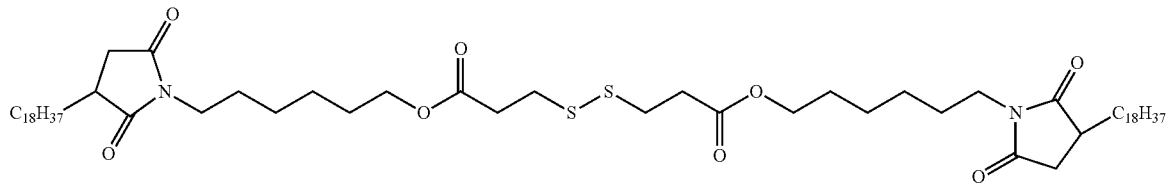

(I-10)

[Chemical Formula 15]

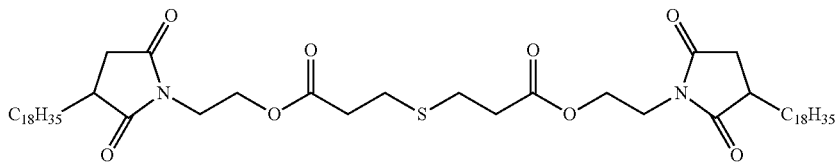

(I-11)

[Chemical Formula 16]

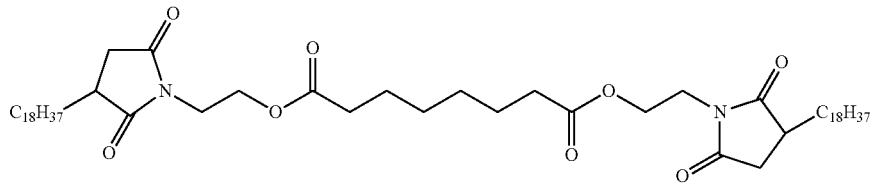

(I-12)

The ester (I) described above may be used without modification as an additive for oils or the like, but may also be converted to a salt or the like prior to use.

Examples of the salt include acid addition salts, amino acid addition salts or the like.

Examples of the acid addition salts include organic acid salts, inorganic acid salts or the like. Specific examples of organic acid salts include carboxylates, sulfonates or the like, preferred examples include formate, acetate, trifluoroacetate, propionate, methanesulfonate, p-toluenesulfonate, trifluoromethanesulfonate salts or the like, and of these, methanesulfonate salts or the like are particularly desirable. Specific examples of inorganic acid salts include hydrochloride, hydrobromide, hydroiodide, nitrate, sulfate, carbonate, borate salts or the like (but excluding phosphate salts), and of these, borate salts or the like are particularly desirable.

Specific examples of amino acid addition salts include addition salts of lysine, glycine, phenylalanine, aspartic acid, glutamic acid or the like.

When it is desirable that the ester (I) is obtained as a salt, the salt may simply be purified in those cases where the ester (I) is obtained in the form of a salt, or in those cases where the ester (I) is obtained in free form, the ester (I) may be dissolved or suspended in an appropriate solvent, and an acid or base added to isolate the salt, which may then be purified.

Further, the ester (I) or salt therefor may sometimes exist as an adduct with water or any of various solvents, and these adducts may also be used as the additive for oils according to the present invention.

The ester (I) includes some compounds that have optionally stereoisomers such as geometric isomers, optical isomers and tautomers, but in the present invention, any of these isomers, including all possible isomeric forms and mixtures thereof, may be used as the additive for oils.

An example of a method of producing the ester (I) is a method that includes reacting a dibasic acid corresponding with the ester and an alcohol, aminoalcohol or the like in the presence of an acid catalyst such as methanesulfonic acid, p-toluenesulfonic acid or the like at a temperature of 100 to 150° C. In other methods, hydrogen chloride or thionyl chloride or the like may be used as the catalyst. In the above method, 2 to 10 equivalents of the alcohol or aminoalcohol are preferably used relative to the dibasic acid, and this amount is more preferably 2 to 5 equivalents of the alcohol or aminoalcohol.

A solvent may be used during the reaction for producing the ester (I), and examples of solvents that may be used include hydrocarbon-based solvents such as decane, tetradecane, toluene, xylene or the like, ether-based solvents such as methoxybenzene, diphenyl ether or the like, halogen-based solvents such as chlorobenzene, dichlorobenzene or the like, amide-based solvents such as N,N-dimethylformamide, N,N-dimethylacetamide or the like, and sulfur-containing solvents such as dimethylsulfoxide or the like.

Specific examples of the dibasic acid corresponding with formula (I) include oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, glutaric acid, 2-methylglutaric acid, 3-methylglutaric acid, 2,2-dimethylglutaric acid, 3,3-dimethylglutaric acid, 2,4-diethylglutaric acid, adipic acid, 3-methyladipic acid, 3-butyladipic acid, pimelic acid, suberic acid, azelaic acid, sebacic acid (decanedioic acid), undecanedioic acid, dodecanedioic acid, hexadecanedioic acid, docosanedioic acid, 2,2'-thiodiglycolic acid, 2,2'-dithiodiglycolic acid, 3,3'-thiodipropionic acid, 3,3'-dithiodipropionic acid, 4,4'-thiodibutyric acid, 4,4'-dithiodibutyric acid or the like.

The majority of the above dibasic acids are available as commercial products, but may also be produced, for example, using the methods disclosed in U.S. Pat. No. 3,231,608 and Japanese Unexamined Patent Application, First Publication No. Hei 11-116550 or the like.

As the alcohol used as a raw material for producing the ester (I), a compound obtained by appending a hydroxyl group to a previously described hydrocarbyl group or the like may be used. Specific examples of such alcohols include linear or branched alkyl alcohols such as methanol, ethanol, propanol, isopropyl alcohol, dodecanol, octadecyl alcohol, isooctadecyl alcohol or the like, alkenyl alcohols (in which there are no particular restrictions on the position of the double bond or on the geometric isomer) such as vinyl alcohol, crotyl alcohol, dodecenyl alcohol, octadecenyl alcohol, isooctadecenyl alcohol or the like, cycloalkyl alcohols such as cyclopropanol, cyclobutanol, cyclohexanol or the like, and aromatic alcohols such as phenol, naphthalene alcohol or the like. These alkyl alcohols or alkenyl alcohols may include an aromatic substituent on any of the carbon atoms within the molecular structure. Further, the cycloalkyl alcohols and aromatic alcohols have optionally a hydrocarbyl group substituent on any of the carbon atoms within the molecular structure.

Examples of the aminoalcohol used as a raw material for producing the ester (I) include primary aminoalcohols, mono- or di-N-hydrocarbyl-substituted aminoalcohols, mono- or di-N-hydrocarbylcarbonyl-substituted aminoalcohols, hydrocarbyl aldehyde iminoalcohols, imido-N-hydrocarbyl alcohols or the like.

As the primary aminoalcohol, a compound obtained by appending a hydroxyl group and an amino group to a previously described hydrocarbylene group may be used. Specific examples of such primary aminoalcohols include ethanolamine, 2-amino-1-propanol, 1-amino-2-propanol, 3-amino-1-propanol, 1-amino-2-butanol, 2-amino-1-butanol, 4-amino-1-butanol, 2-amino-2-methylpropanol, 3-amino-2,2-dimethyl-1-propanol, 4-amino-2-methyl-1-butanol, 5-aminopentanol, 2-amino-3-methyl-1-butanol, 2-amino-1-pentanol, 6-amino-1-hexanol, 2-amino-4-methyl-1-pentanol, 2-amino-3,3-dimethyl-1-butanol, 2-amino-1-hexanol, 5-amino-2,2-dimethylpentanol, 6-amino-2-methyl-2-heptanol, 8-amino-1-octanol, 10-amino-1-decanol, 12-amino-1-dodecanol, 1-amino-1-cyclopentanemethanol, 2-amino-2-cyclohexyl-1-propanol, aminocyclohexanol, 1-aminomethyl-1-cyclohexanol, 3-aminomethyl-3,5,5-trimethylcyclohexanol, aminophenol, aminobenzyl alcohol, aminophenethyl alcohol, 2-anilinoethanol, 3-(1-hydroxyethyl)aniline, aminomethylbenzyl alcohol, aminocresol, 2-amino-4-tert-butylphenol, 4-amino-2,6-diphenylphenol, N-(4-hydroxyphenyl)-2-naphthylamine, aminonaphthol, aminohydroxyfluorene, 2-amino-1,2-diphenylethanol, aminophenylethanol, phenylglycinol, aminophenylpropanol, 2-amino-1,1-diphenyl-1-propanol or the like. The majority of these amino group-containing alcohols are available as commercial products, but may also be produced, for example, using the methods disclosed in Japanese Unexamined Patent Application, First Publication No. Sho 61-43146 and Polish Journal of Chemistry (Pol. J. Chem.) 521283 (1978) or the like.

The mono- or di-N-hydrocarbyl-substituted aminoalcohols can be obtained either by introducing one or two hydrocarbyl substituents at the nitrogen atom of one of the above primary aminoalcohols, or by introducing a hydrocarbyl alcohol group into a mono- or di-N-hydrocarbyl-substituted amine. A method such as that disclosed in Org. Synth., I, 102 (1941) or the like can be used for achieving the above introductions. Specific examples of these compounds include N-methylhydroxylamine, N,N-dimethylhydroxylamine, N-isopropylhydroxylamine, 2-(methylamino)ethanol, N-tert-butylhydroxylamine, 3-(methylamino)-1-propanol, 2-dimethylaminoethanol, 2-(ethylamino)ethanol, N,N-diethylhydroxylamine, 3-dimethylamino-1-propanol, 1-dimethylamino-2-propanol, 2-(propylamino)ethanol, 2-(tert-butylamino)ethanol, N-n-butylethanolamine, 2-dimethylamino-2-methylpropanol, 2-(diethylamino)ethanol, 2-(butylamino)ethanol, 4-dimethylamino-1-butanol, 4-ethylamino-1-butanol, 3-diethylamino-1-propanol, 1-diethylamino-2-propanol, 3-dimethylamino-2,2-dimethyl-1-propanol, 4-(n-butylamino)-1-butanol, 2-(diisopropylamino)ethanol, 6-dimethylamino-1-hexanol, 2-isopropylamino-3-methyl-1-butanol, 2-(dibutylamino)ethanol, 2-di(n-butylamino)ethanol, 8-dimethylamino-1-octanol, N-cyclohexylhydroxylamine, 1-aziridineethanol, 1-(2-hydroxyethyl)pyrrolidine, 1-piperidineethanol, 2-(N-ethylanilino)ethanol, dimethylaminophenol, diethylaminophenol, diethyltoluidinoethanol, dimethylaminophenethyl alcohol, N-benzylhydroxylamine, norephedrine, 2-(dibutylamino)-1-phenyl-1-propanol, N-methylephedrine, pseudoephedrine, methylpseudoephedrine, N-benzylethanolamine, 2-(benzylamino)cyclohexanemethanol, (methylaminomethyl)benzyl alcohol, ephedrine, 3-(dibenzylamino)-1-propanol, N,N-dibenzylhydroxylamine, N-benzyl-N-methylethanolamine, 2-(dibenzylamino)-3-phenyl-1-propanol, ethylaminocresol or the like.

The mono- or di-N-hydrocarbylcarbonyl-substituted aminoalcohols can be obtained by introducing one or two hydrocarbylcarbonyl substituents at the nitrogen atom of one of the above primary aminoalcohols. A method such as that disclosed in Angew. Chem., 74, 407 (1962) or the like can be used for achieving the above introductions. Specific examples of these hydrocarbylcarbonyl substituents include linear or branched alkylcarbonyl groups such as acetyl, ethylcarbonyl, propylcarbonyl, isopropylcarbonyl, dodecylcarbonyl, heptadecylcarbonyl, isoheptadecylcarbonyl or the like, alkenylcarbonyl groups (in which there are no particular restrictions on the position of the double bond or on the geometric isomer) such as vinylcarbonyl, propenylcarbonyl, butenylcarbonyl, dodecenylcarbonyl, heptadecenylcarbonyl, isoheptadecenylcarbonyl or the like, cycloalkylcarbonyl groups such as cyclopropylcarbonyl, cyclobutylcarbonyl, cyclohexylcarbonyl or the like, and aromatic carbonyl groups such as benzenecarbonyl, naphthalenecarbonyl or the like. These alkylcarbonyl groups and alkenylcarbonyl groups may include an aromatic substituent on any of the carbon atoms within the molecular structure. Further, the cycloalkylcarbonyl groups and aromatic carbonyl groups have optionally a hydrocarbyl group substituent on any of the carbon atoms within the molecular structure.

The mono- or di-N-hydrocarbyloxycarbonyl aminoalcohols can be obtained by introducing one or two hydrocarbyloxycarbonyl substituents at the nitrogen atom of one of the above primary aminoalcohols. Examples of methods of performing these introductions include the same method as that described above for introducing the hydrocarbylcarbonyl substituents, and other conventional methods such as the method disclosed in "Protective Groups in Organic Synthesis", third edition, authored by T. W. Greene, published by John Wiley & Sons Inc. (1999) or the like.

Specific examples of the hydrocarbyloxycarbonyl substituents include benzyloxycarbonyl, p-methoxybenzyloxycarbonyl, tert-butoxycarbonyl, 9-fluorenylmethoxycarbonyl or the like.

The hydrocarbyl aldehyde iminoalcohols can be obtained by a dehydration condensation of an aforementioned primary aminoalcohol and a hydrocarbyl aldehyde. As the condensation method, a method such as that disclosed in J. Org. Chem., 33, 3501 (1968) or the like may be used. Examples of preferred hydrocarbyl aldehydes include linear or branched alkyl aldehydes such as acetaldehyde, propanal, butanal, isobutanal, tridecanal, octadecanal, isooctadecanal or the like, alkenyl aldehydes (in which there are no particular restrictions on the position of the double bond or on the geometric isomer) such as acrolein, crotonaldehyde, butenal, dodecenal, heptadecenal, isoheptadecenal or the like, cycloalkyl aldehydes such as cyclopropanal, cyclobutanal, cyclohexanal or the like, and aromatic aldehydes such as benzaldehyde, naphthalenealdehyde or the like. These alkyl aldehydes and alkenyl aldehydes may include an aromatic substituent on any of the carbon atoms within the molecular structure. Further, the cycloalkyl aldehydes and aromatic aldehydes have optionally a hydrocarbyl substituent on any of the carbon atoms within the molecular structure.

The imido-N-hydrocarbyl alcohols can be obtained by a dehydration condensation of an aforementioned primary aminoalcohol and an intramolecular acid anhydride. As the condensation method, a method such as that disclosed in Org. Synth., IV, 106 (1963) or the like may be used. Examples of preferred intramolecular acid anhydrides include butanedioic anhydride, maleic anhydride, succinic anhydride, hexanedioic anhydride, phthalic anhydride or the like. These intramolecular acid anhydrides may be substituted with hydrocarbyl. This hydrocarbyl is as defined above. In the ester (I) described above, the nitrogen substitution method described above may also be used to introduce any of various substituents at the nitrogen atom following the reaction between the dibasic acid and the primary aminoalkanol.

Another method that may be used to produce the ester (I) is a method that includes reacting the dibasic acid corresponding with the ester and the alcohol or aminoalcohol in the presence of a basic compound using a condensation agent at a temperature of 0 to 100° C. In this method, 2 to 10 equivalents of the alcohol or aminoalcohol are preferably used relative to the dibasic acid, and this amount is more preferably 2 to 5 equivalents of the alcohol or aminoalcohol. Further, the basic compound is typically used in an amount of 0.1 to 20 equivalents, and preferably 0.5 to 5 equivalents, whereas the condensation agent is typically used in an amount of 0.1 to 20 equivalents, and preferably 0.5 to 5 equivalents.

Examples of the basic compound include pyridine, lutidine, and amine-based compounds such as 4-dimethylaminopyridine, triethylamine or the like.

Examples of the condensation agent include carbodiimide-based compounds such as 1-ethyl-3-N,N'-dimethylaminopropylcarbodiimide, N,N'-dicyclohexylcarbodiimide or the like.

In each of these production methods, during reaction between the corresponding dibasic acid and the alcohol or aminoalcohol, if required, a protective group may be introduced at the amino group of the aminoalcohol, with this protective group then being suitably eliminated following completion of the reaction.

The introduction and elimination of a protective group at an active group may be performed using conventional methods [such as the methods disclosed in "Protective Groups in Organic Synthesis", third edition, authored by T. W. Greene, published by John Wiley & Sons Inc. (1999) or the like].

If the ester (I) described above is used as an additive for oils, then because the ester is capable of imparting wear resistance properties or friction resistance properties to oils such as lubricant base oils or fuel oils, it can be used instead of the conventionally employed friction modifiers (friction reducers and oiliness agents), wear reducers (includes extreme pressure agents and seizure preventive agents or the like) described below or the like. Further, although wear resistance properties or friction resistance properties can be imparted using only the ester (I), in some cases conventional friction modifiers, wear reducers or the like may be used in combination with the ester (I).

Moreover, mixtures of two or more of the esters (I) of the present invention having different structures may also be used.

Furthermore, the ester (I) of the present invention not only imparts favorable wear resistance properties or friction resistance properties, but also exhibits excellent solubility in oils such as lubricant base oils and fuel oils, and adding the ester to these types of oils enables favorable oxidation stability, corrosion resistance, rust preventing properties, antifoaming properties or the like to be imparted.

A lubricant of the present invention contains a lubricant base oil and an additive for oils containing the aforementioned ester (I). The amount of the ester (I) within the lubricant is preferably within a range from 0.001 to 300 mmol, more preferably from 0.01 to 200 mmol, and still more preferably from 0.1 to 100 mmol, per 1 kg of the lubricant. Provided the amount of the ester (I) is within this range, satisfactory wear resistance properties or friction resistance properties can be imparted.

As the lubricant base oil, all manner of lubricant base oils, typified by natural base oils, synthetic base oils or the like, may be used. Further, the lubricant base oil may be either a polar base oil or a non-polar base oil.

Examples of natural base oils include mineral oils, vegetable oils, animal oils or the like, and specific examples include paraffin-based crude oils, intermediate base crude oils, naphthene-base crude oils or the like, although this is not an exhaustive list.

Furthermore, solvent-refined oils obtained by using an aromatic extractant such as phenol, furfural or the like to treat a lubricant base oil prepared by distilling the above natural oils at normal pressure or under reduced pressure, hydrocracked oils obtained by bringing the lubricant base oil into contact with hydrogen under severe cracking reaction conditions in the presence of a hydrocracking catalyst, hydrotreated oils obtained by bringing the lubricant base oil into contact with hydrogen under hydrotreatment conditions in the presence of a hydrotreatment catalyst such as cobalt, molybdenum or the like supported on a silica-alumina carrier, and highly purified oils obtained by treating the lubricant base oil using a method that employs multiple hydrotreatments, a hydrotreatment or solvent purification treatment followed by an alkali distillation or sulfuric acid washing treatment, or a catalytic dewaxing treatment followed by a hydrotreatment or the like can also be used favorably.

Examples of vegetable oils include rapeseed oil, sunflower oil, soybean oil, olive oil, palm oil, corn oil or the like, although this is not an exhaustive list.

Examples of synthetic oils include poly-α olefins such as polybutene, polypropylene, α-olefin of 8 to 14 carbon atoms oligomer or the like, esters such as fatty acid monoesters, aromatic monoesters, fatty acid diesters, aromatic diesters, aliphatic polybasic acid esters, aromatic polybasic acid esters, polyol polyesters or the like, as well as polyalkylene glycols, phosphate esters, silicones, silicate esters, polyphenyl ethers, alkylbenzenes, synthetic naphthenes, gas-to-liquid (GTL) products, fluorocarbons, ionic liquids or the like, although this is not an exhaustive list.

Of these, preferred lubricant base oils include solvent-refined oils, hydrocracked oils, highly refined oils, vegetable oils, poly-α olefins, aliphatic esters (such as fatty acid monoesters, fatty acid diesters, aliphatic polybasic acid esters and polyol polyesters), polyalkylene glycols, phosphate esters, silicones, silicate esters, polyphenyl ethers, alkylbenzenes, synthetic naphthenes and gas-to-liquid (GTL) products, and one or more of these oils is preferably used.

Besides the aforementioned lubricant base oil and the additive for oils containing the ester (I), the lubricant of the present invention may also contain, as optional components, detergent dispersants, antioxidants, wear reducers (wear resistance agents, seizure prevention agents and extreme pressure agents), friction modifiers, oiliness agents, rust preventative agents, vapor phase rust preventative agents, pour point depressants, viscosity index improvers, thickeners, preservatives, antifoaming agents, demulsifying agents, dyes and fragrances. Although there are no particular limitations on the amounts added of these additives, the amount of each additive within the lubricant base oil is preferably within a range from 0.001 to 5% by weight.

Detergent dispersants are additives that are used mainly to provide a dispersion effect which stably disperses the sludge that generates within the oil over time and suppresses the occurrence of such aggregated deposits, a solubilization effect which solubilizes unstable intermediates such as water, organic acids, sludge precursors or the like, thereby inhibiting growth of varnish and/or sludge, and an acid neutralization effect which neutralizes organic acids or sulfuric acid generated by degradation of the lubricant base oil or additives, thereby inhibiting substrate corrosion and the wear caused by such corrosion. Detergent dispersants can be broadly classified into metal-based detergents that contain a metal, and ashless dispersants that contain no metal. Representative examples of the former include colloids prepared by dispersing a metal hydroxide or carbonate in a neutral or basic sulfonate, overbased sulfonate, overbased phenate, overbased salicylate, phosphonate, overbased carboxylate or the like. Examples of the metal include calcium, magnesium, barium or the like. Examples of the ashless dispersants include mono-succinimides, bis-succinimides or the like. As the detergent dispersant, any of the above dispersants may be used alone, or a combination of two or more different dispersants may be used.

Antioxidants are additives that are used mainly for inhibiting the degradation and decomposition that occurs when the lubricant base oil or additives react with oxygen in the air. These antioxidants function as chain transfer reaction terminators, as decomposition agents for peroxides, and as deactivators for metal compounds that can act as oxidation catalysts. Examples of antioxidants that function as chain terminators include phenol-based compounds, aromatic amine-based compounds or the like. Examples of antioxidants that function as peroxide decomposition agents include sulfur-based compounds, sulfur-phosphorus-based compounds or the like.

Examples of metal deactivators include compounds such as benzotriazole that have the ability to form complexes with metals. As the antioxidant, any of these compounds may be used alone, or a combination of two or more different antioxidants may be used.

Wear reducers are additives that are used mainly for reducing wear and preventing seizure at a friction surface generated by relative movement, by forming a film of an inorganic compound at the friction surface by chemically reacting with the metal or meal oxide that forms the friction surface. Compounds that inhibit wear are termed wear resistance agents, compounds that prevent seizure are termed seizure prevention agents, and compounds that prevent seizure and inhibit wear under the types of severe conditions that can lead to seizure are termed extreme pressure agents. Wear reducers can be broadly classified into sulfur-based compounds, phosphorus-based compounds, chlorine-based compounds and organometallic compounds. The sulfur-based compounds include sulfurized olefins, sulfides or the like, and are typified by dibenzyl disulfide (DBDS). The phosphorus-based compounds include phosphites, phosphates, aminephosphates or the like, and are typified by tricresyl phosphate (TCP). An example of the chlorine-based compounds is chlorinated paraffin or the like. Representative examples of the organometallic compounds include zinc dialkyldithiophosphate (ZnDTP), zinc dialkyldithiocarbamate (ZnDTC), molybdenum dialkyldithiocarbamate (MoDTC), molybdenum dialkyldithiophosphate (MoDTP) or the like. As the wear reducer, any of these compounds may be used alone, or a combination of two or more different compounds may be used.

When an additive for oils of the present invention containing the ester (I) is used, these sulfur-based, phosphorus-based, chlorine-based or organometallic wear reducers may be used in combination, but if the additive for oils of the present invention is used, then excellent wear resistance properties or friction resistance properties can be imparted to oils such as lubricant base oils even without the use of these conventional wear reducers. Accordingly, increases in the concentration of the metal fraction and/or phosphorus fraction within the oil caused by adding these conventional phosphorus-based or organometallic wear reducers can be prevented.

Friction modifiers are additives that are used mainly for reducing or increasing friction at a friction surface generated by relative movement, by undergoing physical adsorption or chemical adsorption to the metal or meal oxide that forms the friction surface. Compounds whose main purpose is to reduce friction are also termed oiliness agents or friction reducers. Friction modifiers can be broadly classified into ashless friction modifiers that contain no metal, metal-based friction modifiers that contain a metal, and solid lubricants. Ashless friction modifiers have a structure that combines a polar group that can bond strongly to metal surfaces and a long carbon chain within the same molecule, and are typified by stearic acid, oleic acid, stearylamine, oleyl alcohol, oleylamine, oleylamide, and glycerol monooleate (GMO) or the like. Examples of the metal-based friction modifiers include MoDTC, MoDTP or the like. Examples of the solid lubricants include graphite, molybdenum disulfide or the like. As the friction modifiers, any of these compounds may be used alone, or a combination of two or more different compounds may be used.

When an additive for oils of the present invention containing the ester (I) is used, friction modifiers such as the above ashless friction modifiers, metal-based friction modifiers, solid lubricants or the like may be used in combination, but if the additive for oils of the present invention is used, then excellent wear resistance properties or friction resistance properties can be imparted to oils such as lubricant base oils even without the use of these conventional friction modifiers. Accordingly, increases in the concentration of the metal fraction within the oil caused by adding these conventional metal-based friction modifiers can be prevented.

Rust preventative agents are additives that are used mainly for preventing substrate rusting caused mainly by oxygen and moisture in the air. Examples of the rust preventative agents include alkylsuccinic acid derivatives, metal soaps, esters, sulfonates, phosphites, amines or the like.

Pour point depressants are additives that are used for improving the low-temperature fluidity, and thereby lowering the minimum usable temperature for the lubricant base oil, by further lowering the wax pour point of the lubricant base oil. Representative examples of such pour point depressants include polyalkyl methacrylates, polyalkyl acrylates, polyvinyl acetate, polyalkylstylenes, polybutene, condensates of chlorinated paraffin and naphthalene, condensates of chlorinated paraffin and phenol or the like.

Viscosity index improvers are additives that are used mainly for increasing the viscosity index, thereby reducing the viscosity variation upon temperature changes, and further widening the usable temperature range for the lubricant base oil. Representative examples of such viscosity index improvers include polyalkyl methacrylates, polyisobutylene, polyalkylstyrenes, ethylene-propylene copolymers, styrene-hydrogenated diene copolymers, styrene-maleic anhydride ester copolymers or the like.

Antifoaming agents are additives that are used mainly for preventing mechanical malfunctions, lubricant base oil overflow and/or oxidation-degradation acceleration caused by the wear or seizure that accompanies oil loss or compression increase arising mainly as a result of foaming of the lubricant base oil. Representative examples of such antifoaming agents include dimethylsiloxanes, fluorosilicones, polyacrylates, perfluoroalkyl ethers or the like.

These rust preventative agents, pour point depressants, viscosity index improvers and antifoaming agents may each employ either one of the exemplified compounds or a combination of two or more compounds.

The lubricant of the present invention can be used in all manner of applications, including engine oils, automatic transmission oils, continuously variable transmission oils, gear oils, power steering oils, shock absorber oils, turbine oils, hydraulic oils, refrigerating machine oils, rolling oils, bearing oils, metalworking lubricants, sliding surface oils, greases, biolubricants or the like.

As described above, the additive for oils containing the ester (I) imparts favorable wear resistance properties or friction resistance properties to the lubricant base oil without containing a metal fraction or a phosphorus fraction. Accordingly, the additive is extremely favorable from an environmental perspective, and is also extremely useful in those applications where the use of conventional additives having a heavy metal fraction containing zinc or molybdenum or a phosphorus fraction are carefully restricted due to concerns relating to adverse effects on humans or contamination of the lubricant base oil (including applications such as mechanical machinery such as conveyors or medical equipment used during food processing or drug manufacture or the like)

Furthermore, addition of the additive for oils containing the ester (I) can be used to impart favorable wear resistance properties or friction resistance properties regardless of whether the lubricant base oil is a polar base oil or a non-polar base oil.

The additive for oils of the present invention can be added not only to lubricant base oils, but also to other oils such as fuel oils.

Examples of fuel oils include highly hydrorefined high-performance turbine fuel oils, and biodiesel produced by treating and purifying vegetable oils, animal oils or waste edible oils. However, these highly hydrorefined fuel oils tend to suffer from particularly inadequate lubrication performance, and fuel pumps using these types of fuel oils are prone to wear. Further, biodiesel fuel oil is highly polar, and in these types of fuel oils, conventional oil additives have been unable to ensure satisfactory performance. Accordingly, the additive for oils of the present invention is extremely useful. The amount of the ester (I) is typically within a range from 0.00001 to 10% by mass, preferably from 0.00001 to 5% by mass, and still more preferably from 0.00001 to 1% by mass, relative to 100% by mass of the fuel oil. Provided the amount of the ester (I) is within this range, more effective wear resistance properties or more effective friction resistance properties can be imparted to the oil. In such cases, the fuel oil may also include all manner of other additives in addition to the additive for oils of the present invention.

Furthermore, besides the properties described in the present invention, the additive for oils of the present invention also exhibits excellent solubility and heat-resistant stability within base oils, and exhibits superior levels of the various properties required of extreme pressure agents, corrosion prevention agents, rust preventative agents and antioxidants and the like that are used as lubricant additives. Further, the additive for oils of the present invention can also be used as an oil additive, such as an oiliness agent, friction modifier or wear reducer or the like, for members that use nonferrous metals such as aluminum or members that use dissimilar metals such as a nonferrous metal and iron.

Furthermore, the additive for oils of the present invention can also be used as an emulsifier, solubilizer, dispersant or plasticizer for cosmetic products, pharmaceutical products, fertilizers, biomaterials, electronic equipment materials, coating materials, inks, printing materials, foodstuffs or the like, or as a lubricant for synthetic resins or a component of hair cosmetic products, gelling agents, paper additives, crystal nucleation agents or the like.

EXAMPLES

A more detailed description of the present invention is presented below based on a series of examples.

The measurement data reported in the examples were obtained using the measuring apparatus and measuring techniques described below.

(1) Nuclear magnetic resonance spectra ($^1$H-NMR: conducted using tetramethylsilane as a standard): GSX-400 (400 MHz) (manufactured by JEOL Ltd.)

(2) High performance liquid chromatography (apparatus: Shimadzu C-R4A, column: YMC Pack Ph A-414 ϕ6.0×300 mm, mobile phase: tetrahydrofuran/0.1% aqueous solution of phosphoric acid=7/3, column temperature: 40° C., flow rate: 0.7 ml/minute, detector: UV (220 nm), sample concentration: 10 g/L, injection volume: 5 µL)

(3) Measurement of coefficient of kinetic friction (evaluation of friction resistance property): Soda pendulum-type friction tester (manufactured by Shinko Engineering Co., Ltd.)

(4) Measurement of wear scar diameter (evaluation of wear resistance property): Shell-type four-ball friction tester (manufactured by Takachiho Seiki Co., Ltd.)

(5) Evaluation of heat resistance and oxidation resistance stability of lubricant compositions: lubricant oxidation stability tester for internal combustion engine (Rigo Co., Ltd.)

Synthesis Example 1

N-(2-hydroxyethyl)octadecyl succinimide

A 50 mL reaction flask was charged with 17.6 g of octadecyl succinic anhydride (manufactured by Tokyo Chemical Industry Co., Ltd.) and 3.1 g of ethanolamine (manufactured by Tokyo Chemical Industry Co., Ltd.), and the resulting mixture was reacted at 160° C. for 4 hours under continuous nitrogen purging and with vigorous stirring. The reaction product was purified by silica gel column chromatography (mobile phase: ethyl acetate/hexane), yielding 10.6 g of N-(2-hydroxyethyl)octadecyl succinimide (yield: 54%).

High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 3H), 1.26 (m, 32H), 1.51 (m, 1H), 1.92 (m, 1H), 2.19 (t, 1H), 2.42 (dd, 1H), 2.83 (m, 1H), 2.87 (dd, 1H), 3.73 (m, 2H), 3.78 (m, 2H)

Synthesis Example 2

N-(2-hydroxyethyl)-9-octadecenyl succinimide

A 50 mL reaction flask was charged with 35.1 g of octadecenyl succinic anhydride (manufactured by Tokyo Chemical Industry Co., Ltd.) and 6.1 g of ethanolamine (manufactured by Tokyo Chemical Industry Co., Ltd.), and the resulting mixture was reacted at 110° C. for 6 hours under continuous nitrogen purging and with vigorous stirring. The reaction product was purified by silica gel column chromatography (mobile phase: ethyl acetate/hexane), yielding 29.6 g of N-(2-hydroxyethyl)-9-octadecenyl succinimide (yield: 75.3%).

High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 3H), 1.26 (m, 26H), 1.98 (dt, 2H), 2.18 (t, 1H), 2.33 (m, 1H), 2.49 (dd, 1H), 2.54 (m, 1H), 2.79 (dd, 1H), 2.91 (m, 1H), 3.72 (m, 2H), 3.76 (m, 2H), 5.28 (m, 1H), 5.55 (m, 1H)

Synthesis Example 3

N-(6-hydroxyhexyl)octadecyl succinimide

A 300 mL reaction flask was charged with 63.2 g of octadecyl succinic anhydride (manufactured by Tokyo Chemical Industry Co., Ltd.) and 21.0 g of 6-amino-1-hexanol (manufactured by Tokyo Chemical Industry Co., Ltd.), and the resulting mixture was reacted at 160° C. for 3.5 hours under continuous nitrogen purging and with vigorous stirring. The reaction product was purified by silica gel column chromatography, yielding 55.87 g of N-(6-hydroxyhexyl)octadecyl succinimide (yield: 69.0%).

High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 3H), 1.20 to 1.63 (m, 42H), 1.89 (m, 1H), 2.36 (m, 1H), 2.80 (m, 2H), 3.49 (t, 2H), 3.63 (t, 2H)

Example 1 di(6-aminohexyl) 3,3'-thiodipropionate (ester (I-1))

8.1 g of methanesulfonic acid (manufactured by Wako Pure Chemical Industries, Ltd.) was added dropwise, under an atmosphere of nitrogen and at 70° C., to 9.4 g of 6-amino-1-hexanol (manufactured by Tokyo Chemical Industry Co., Ltd.). After stirring for 10 minutes, 7.1 g of 3,3'-thiodipropionic acid (manufactured by Wako Pure Chemical Industries, Ltd.) was added, and the resulting mixture was heated to 120° C. and then stirred at 110° C. for 7 hours. Following completion of the reaction, the reaction mixture was cooled to room temperature and then added gradually to 50 mL of methyl isobutyl ketone (manufactured by Wako Pure Chemical Industries, Ltd.). After stirring for 2 hours, the precipitated crystals were collected by filtration and washed with acetone, yielding the methanesulfonate salt of di(6-aminohexyl) 3,3'-thiodipropionate.

11.2 g of the obtained methanesulfonate salt was dissolved uniformly in 500 mL of methylene chloride, the organic layer was washed with a 1.0% by weight aqueous solution of sodium bicarbonate and then with distilled water, and was then dried over anhydrous magnesium sulfate, before the solvent was removed by distillation at 50° C., yielding 0.5 g of the ester (I-1) (yield: 6.8%). The physical properties of the ester were as listed below.

$^1$H-NMR (CDCl$_3$, δ ppm): 1.37 (m, 8H), 1.47 (m, 4H), 1.67 (m, 8H), 2.61 (t, 4H), 2.70 (t, 4H), 2.81 (t, 4H), 4.10 (t, 4H)

Elemental analysis result: $C_{18}H_{36}N_2O_4S$

Calculated values (C: 57.41%, H: 9.64%, N: 7.44%, S: 8.52%)

Measured values (C: 57.70%, H: 9.71%, N: 7.20%, S: 8.39%)

(1) Measurement of Coefficient of Kinetic Friction (Evaluation of Friction Resistance Properties)

Using the ester (I-1) as an oil additive, the ester was added to samples of a poly-α-olefin (DURASYN164, manufactured by INEOS Group Ltd., lubricant base oil A) and di(3,5,5-trimethylhexyl) adipate (lubricant base oil B) in an amount equivalent to 10 mmol/kg, thus completing preparation of lubricant sample oils.

Subsequently, the coefficient of kinetic friction of each of these lubricant sample oils at 40° C. and 80° C. was measured using a Soda pendulum-type friction tester (manufactured by Shinko Engineering Co., Ltd.). The coefficient of kinetic friction was calculated from the initial amplitude of the pendulum, the amplitude upon oscillation, and the oscillation frequency. The results are shown in Table 1.

(2) Measurement of Wear Scar Diameter (Evaluation of Wear Resistance Properties)

Sample oils were prepared in the same manner as (1) described above, and testing was conducted in accordance with the method prescribed in ASTM D4172 (loading: 40 kgf, revolution rate: 1,200 rpm, time: 60 minutes, temperature: 75° C.). The diameter of the wear scar was measured following completion of the testing. A shell-type four-ball friction tester (manufactured by Takachiho Seiki Co., Ltd.) was used as the test apparatus. The wear scar diameter was taken as the average of the wear scars in the vertical direction and the horizontal direction on the three fixed balls. The results are shown in Table 1.

Example 2 di(6-aminohexyl) 3,3'-dithiodipropionate (ester (I-2))

2.0 g of methanesulfonic acid (manufactured by Wako Pure Chemical Industries, Ltd.) was added dropwise, under an atmosphere of nitrogen and at 70° C., to 2.3 g of 6-amino-1-hexanol (manufactured by Tokyo Chemical Industry Co., Ltd.). After stirring for 10 minutes, 2.1 g of 3,3'-dithiodipropionic acid (manufactured by Wako Pure Chemical Industries, Ltd.) was added, and the resulting mixture was heated to 120° C. and then stirred at 110° C. for 3 hours. Following completion of the reaction, the reaction mixture was cooled to room temperature and then added gradually to 50 mL of methyl isobutyl ketone (manufactured by Wako Pure Chemical Industries, Ltd.). After stirring for 2 hours, the precipitated crystals were collected by vacuum filtration and washed with acetone, yielding the methanesulfonate salt of di(6-aminohexyl) 3,3'-dithiodipropionate.

5.0 g of the obtained methanesulfonate salt was dissolved uniformly in 100 mL of methylene chloride, and the organic layer was washed with a 1.0% by weight aqueous solution of sodium bicarbonate and then washed with distilled water. The organic layer was dried over anhydrous magnesium sulfate, and the solvent was then removed by distillation at 50° C., yielding 0.4 g of the ester (I-2) (yield: 10.8%). The physical properties of the ester were as listed below.

$^1$H-NMR (CDCl$_3$, δ ppm): 1.36 (m, 8H), 1.48 (m, 8H), 1.65 (m, 4H), 2.67 to 2.75 (m, 8H), 2.93 (t, 4H), 4.10 (t, 4H)

Elemental analysis result: $C_{18}H_{36}N_2O_4S_2$

Calculated values (C: 52.91%, H: 8.88%, N: 6.86%, S: 15.69%)

Measured values (C: 53.11%, H, 9.00%, N: 6.73%, S: 15.45%)

With the exception of using the ester (I-2) obtained in the manner described above as the oil additive, sample oils were prepared in the same manner as example 1, and then evaluated in the same manner as example 1. The results are shown in Table 1.

Example 3 di[6-(N,N-diethyl)aminohexyl]3,3'-dithiodipropionate (ester (I-3))

7.0 g of 6-amino-1-hexanol (manufactured by Tokyo Chemical Industry Co., Ltd.), 28.1 g of ethyl iodide (manufactured by Wako Pure Chemical Industries, Ltd.) and 12.4 g of potassium carbonate (manufactured by Wako Pure Chemical Industries, Ltd.) were dissolved in 30 mL of methanol (manufactured by Nacalai Tesque, Inc.) and 30 mL of distilled water, and reaction was conducted at 60° C. for 6 hours. Following completion of the reaction, the solvent was removed by distillation, and a distillation was then performed under reduced pressure at 1 Torr and a bath temperature of 150° C., yielding 3.3 g of 6-(N,N-diethyl)amino-1-hexanol (yield: 31.5%).

1.3 g of methanesulfonic acid (manufactured by Wako Pure Chemical Industries, Ltd.) was added dropwise, under an atmosphere of nitrogen and at 70° C., to 2.3 g of the obtained 6-(N,N-diethyl)amino-1-hexanol. After stifling for 10 minutes, 1.4 g of 3,3'-dithiodipropionic acid (manufactured by Wako Pure Chemical Industries, Ltd.) was added, and the resulting mixture was heated to 120° C. and then stirred at 110° C. for 4 hours. Following completion of the reaction, the reaction mixture was cooled to room temperature and then added gradually to 50 mL of methyl isobutyl ketone (manufactured by Wako Pure Chemical Industries, Ltd.). After stirring for 2 hours, the precipitated crystals were collected by filtration and washed with acetone, yielding the methanesulfonate salt of di[6-(N,N-diethyl)aminohexyl]3,3'-dithiodipropionate.

4.7 g of the obtained methanesulfonate salt was dissolved uniformly in 200 mL of methylene chloride, and the organic layer was washed with a 1.0% by weight aqueous solution of sodium bicarbonate and then washed with distilled water. The organic layer was dried over anhydrous magnesium sulfate, and the solvent was then removed by distillation at 50° C., yielding 1.0 g of the ester (I-3) (yield: 28.9%). The physical properties of the ester were as listed below.

$^1$H-NMR (CDCl$_3$, δ ppm): 1.06 (t, 12H), 1.36 (m, 8H), 1.50 (m, 4H), 1.66 (m, 4H), 2.47 (m, 4H), 2.57 (m, 8H), 2.73 (m, 4H), 2.93 (m, 4H), 4.10 (t, 4H)

Elemental analysis result: $C_{26}H_{52}N_2O_4S_2$

Calculated values (C: 59.96%, H: 10.06%, N: 5.38%, S: 12.31%)

Measured values (C: 60.15%, H: 10.13%, N: 5.44%, S: 12.09%)

With the exception of using the ester (I-3) obtained in the manner described above as the oil additive, sample oils were prepared in the same manner as example 1, and then evaluated in the same manner as example 1. The results are shown in Table 1.

Example 4 di(6-aminohexyl) 4,4'-dithiodibutyrate (ester (I-4))

5.1 g of methanesulfonic acid (manufactured by Wako Pure Chemical Industries, Ltd.) was added dropwise, under an atmosphere of nitrogen and at 70° C., to 5.9 g of 6-amino-1-hexanol. After stirring for 10 minutes, 6.0 g of 4,4'-dithiodibutyric acid (manufactured by Tokyo Chemical Industry Co., Ltd.) was added, and the resulting mixture was heated to 120° C. and then stirred at 110° C. for 4 hours. Following completion of the reaction, the reaction mixture was cooled to room temperature and then added gradually to 50 mL of methyl isobutyl ketone (manufactured by Wako Pure Chemical Industries, Ltd.). After stirring for 2 hours, the precipitated crystals were collected by filtration and washed with acetone, yielding the methanesulfonate salt of di(6-aminohexyl) 4,4'-dithiodibutyrate.

3.0 g of the obtained methanesulfonate salt was dissolved uniformly in 100 mL of chloroform, and the organic layer was washed with a 1.0% by weight aqueous solution of sodium bicarbonate and then with distilled water, and was then dried over anhydrous magnesium sulfate, before the solvent was removed by distillation at 50° C., yielding 1.0 g of the ester (I-4) (yield: 49.8%). The physical properties of the ester were as listed below.

$^1$H-NMR (CDCl$_3$, δ ppm): 1.35 to 1.45 (m, 16H), 1.64 (m, 4H), 2.02 (m, 4H), 2.44 (t, 4H), 2.67 to 2.74 (m, 8H), 4.07 (t, 4H)

Elemental analysis result: C$_{20}$H$_{40}$N$_2$O$_4$S$_2$

Calculated values (C: 55.01%, H: 9.23%, N: 6.42%, S: 14.69%)

Measured values (C: 55.15%, H: 9.33%, N: 6.30%, S: 14.48%)

With the exception of using the ester (I-4) obtained in the manner described above as the oil additive, sample oils were prepared in the same manner as example 1, and then evaluated in the same manner as example 1. The results are shown in Table 2.

Example 5 di(2-aminohexyl) 3,3'-dithiodipropionate (ester (I-5))

6.1 g of methanesulfonic acid (manufactured by Wako Pure Chemical Industries, Ltd.) was added dropwise, under an atmosphere of nitrogen and at 70° C., to 7.0 g of 2-amino-1-hexanol (manufactured by Aldrich Co., Ltd.). After stifling for 10 minutes, 6.3 g of 3,3'-dithiodipropionic acid (manufactured by Wako Pure Chemical Industries, Ltd.) was added, and the resulting mixture was heated to 120° C. The mixture was then stirred at 120 to 129° C. for a further 3 hours. Following completion of the reaction, the reaction mixture was cooled to room temperature and then added gradually to 100 mL of methyl isobutyl ketone (manufactured by Wako Pure Chemical Industries, Ltd.). After stifling for 1 hour, the precipitated crystals were collected by filtration and dried at 50° C., yielding the methanesulfonate salt of di(2-amino-hexyl) 3,3'-dithiodipropionate.

1.0 g of the obtained methanesulfonate salt was dissolved uniformly in 50 mL of methylene chloride, and the organic layer was washed with a 1.0% by weight aqueous solution of sodium bicarbonate and then with distilled water, and was then dried over anhydrous magnesium sulfate, before the solvent was removed by distillation at 50° C., yielding 0.2 g of the ester (I-5) (yield: 30.9%). The physical properties of the ester were as listed below.

$^1$H-NMR (CDCl$_3$, δ ppm): 0.90 (t, 6H), 1.33 (m, 8H), 1.47 to 1.55 (m, 4H), 2.62 (m, 4H), 2.96 to 3.30 (m, 6H), 3.52 to 3.71 (m, 4H), 3.96 (m, 2H), 6.37 (m, 2H)

Elemental analysis result: C$_{18}$H$_{36}$N$_2$O$_4$S$_2$

Calculated values (C: 52.91%, H: 8.88%, N: 6.86%, S: 15.69%)

Measured values (C: 52.88%, H: 8.95%, N: 6.81%, S: 15.72%)

With the exception of using the ester (I-5) obtained in the manner described above as the oil additive, sample oils were prepared in the same manner as example 1, and then evaluated in the same manner as example 1. However, only the lubricant base oil B was used as the lubricant base oil. The results are shown in Table 2.

Example 6 di(6-aminohexyl) suberate (ester (I-6))

6.0 g of methanesulfonic acid (manufactured by Wako Pure Chemical Industries, Ltd.) was added dropwise, under an atmosphere of nitrogen and at 70° C., to 7.0 g of 6-amino-1-hexanol (manufactured by Tokyo Chemical Industry Co., Ltd.). After stirring for 10 minutes, 5.2 g of suberic acid (manufactured by Wako Pure Chemical Industries, Ltd.) was added, and the resulting mixture was heated to 120° C. and then stirred at 110° C. for 4 hours. Following completion of the reaction, the reaction mixture was cooled to room temperature and then added gradually to 50 mL of methyl isobutyl ketone (manufactured by Wako Pure Chemical Industries, Ltd.). After stirring for 2 hours, the precipitated crystals were collected by filtration and washed with acetone, yielding the methanesulfonate salt of di(6-aminohexyl) suberate.

8.0 g of the obtained methanesulfonate salt was dissolved uniformly in 500 mL of methylene chloride, and the organic layer was washed with a 1.0% by weight aqueous solution of sodium bicarbonate and then with distilled water, and was then dried over anhydrous magnesium sulfate, before the solvent was removed by distillation at 50° C., yielding 2.0 g of the ester (I-6) (yield: 37.9%). The physical properties of the ester were as listed below.

$^1$H-NMR (CDCl$_3$, δ ppm): 1.36 (m, 4H), 1.46 (m, 8H), 1.64 (m, 4H), 2.67 to 2.75 (m, 8H), 2.93 (t, 4H), 4.10 (t, 4H)

Elemental analysis result: C$_{20}$H$_{40}$N$_2$O$_4$

Calculated values (C: 64.48%, H: 10.82%, N: 7.52%)

Measured values (C: 64.38%, H: 10.80%, N: 7.32%)

With the exception of using the ester (I-6) obtained in the manner described above as the oil additive, sample oils were prepared in the same manner as example 1, and then evaluated in the same manner as example 1. The results are shown in Table 2.

Example 7 di(2-aminohexyl) N,N'-dioleoyl-3,3'-dithiodipropionate (ester (I-7))

2.2 g of the di(2-aminohexyl) 3,3'-dithiodipropionate (ester (I-5)) obtained in example 5 and 1.6 g of triethylamine (manufactured by Wako Pure Chemical Industries, Ltd.) were dissolved in 50 mL of methylene chloride (manufactured by Wako Pure Chemical Industries, Ltd.), 2.9 g of oleic acid chloride (manufactured by Tokyo Chemical Industry Co., Ltd.) was added dropwise to the solution under an atmosphere of nitrogen, and the resulting mixture was stirred for 2 hours at room temperature. Following completion of the reaction, the reaction solution was washed sequentially with distilled water, 0.5 mol/L hydrochloric acid, a saturated aqueous solution of sodium bicarbonate, and a saturated saline solution. The organic layer was then dried over anhydrous magnesium sulfate, and the solvent was removed by distillation at 50° C., yielding 4.3 g of the ester (I-7) (yield: 85.5%). The physical properties of the ester were as listed below.

$^1$H-NMR (CDCl$_3$, δ ppm): 0.89 (t, 12H), 1.28 (m, 48H), 1.50 (m, 4H), 1.62 (m, 4H), 2.02 (m, 8H), 2.32 (t, 4H), 2.57 (t, 4H), 3.00 (t, 4H), 4.07 (m, 2H), 4.15 (m, 4H), 5.35 (m, 4H), 5.93 (dd, 2H)

Elemental analysis result: C$_{54}$H$_{100}$N$_2$O$_6$S$_2$

Calculated values (C: 69.18%, H: 10.75%, N: 2.99%, S: 6.84%)

Measured values (C: 69.14%, H: 10.85%, N: 2.89%, S: 6.70%)

With the exception of using the ester (I-7) obtained in the manner described above as the oil additive, sample oils were prepared in the same manner as example 1, and then evaluated in the same manner as example 1. The results are shown in Table 3.

Example 8

Ester formed from 3,3'-dithiodipropionic acid and N-hydroxyethyloctadecyl succinimide (ester (I-8))

To 8.0 g of the N-(2-hydroxyethyl)octadecyl succinimide obtained in synthesis example 1 were added, under an atmosphere of nitrogen, 2.7 g of 4-dimethylaminopyridine, 2.1 g of 3,3'-dithiodipropionic acid (manufactured by Wako Pure Chemical Industries, Ltd.), 4.3 g of water-soluble carbodiimide hydrochloride and 120 ml of methylene chloride, and the resulting mixture was stirred at a temperature between room temperature and 40° C. for 5.7 hours. Following completion of the reaction, the reaction mixture was washed twice with 50 ml samples of a 0.5 N aqueous solution of hydrochloric acid, once with 100 ml of a 5% aqueous solution of sodium bicarbonate, and then twice with 100 ml samples of pure water, and the organic layer was then separated. The thus obtained organic layer was dried over anhydrous magnesium sulfate and filtered, and the filtrate was then concentrated using a rotary evaporator. The resulting residue was purified by silica gel column chromatography (mobile phase: ethyl acetate/hexane), and the solvent was then removed to obtain 9.6 g of a white solid (yield: 99%). High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 6H), 1.27 (m, 64H), 1.45 (m, 2H), 1.91 (m, 2H), 2.40 (m, 2H), 2.70 (t, 4H), 2.85 (m, 8H), 3.76 (t, 4H), 4.27 (t, 4H)

With the exception of using the ester (I-8) obtained in the manner described above as the oil additive, sample oils were prepared in the same manner as example 1, and then evaluated in the same manner as example 1. The results are shown in Table 3.

Example 9

Ester formed from 3,3'-dithiodipropionic acid and N-hydroxyethyloctadecenyl succinimide (ester (I-9))

To 8.0 g of the N-(2-hydroxyethyl)octadecenyl succinimide obtained in synthesis example 2 were added, under an atmosphere of nitrogen, 2.7 g of 4-dimethylaminopyridine, 2.1 g of 3,3'-dithiodipropionic acid (manufactured by Wako Pure Chemical Industries, Ltd.), 4.3 g of water-soluble carbodiimide hydrochloride and 120 ml of methylene chloride, and the resulting mixture was stirred at a temperature between room temperature and 40° C. for 4.3 hours. Following completion of the reaction, the reaction mixture was washed twice with 50 ml samples of a 0.5N aqueous solution of hydrochloric acid, once with 100 ml of a 5% aqueous solution of sodium bicarbonate, and then twice with 100 ml samples of pure water, and the organic layer was then separated. The thus obtained organic layer was dried over anhydrous magnesium sulfate and filtered, and the filtrate was then concentrated using a rotary evaporator. The resulting residue was purified by silica gel column chromatography (mobile phase: ethyl acetate/hexane), and the solvent was then removed to obtain 7.4 g of a white solid (yield: 80%). High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 6H), 1.27 (m, 52H), 2.00 (m, 4H), 2.30 (m, 2H), 2.45 (m, 2H), 2.55 (m, 2H), 2.72 (m, 6H), 2.90 (m, 6H), 3.67 (t, 4H), 4.27 (t, 4H), 5.38 (m, 2H), 5.56 (t, 2H)

With the exception of using the ester (I-9) obtained in the manner described above as the oil additive, sample oils were prepared in the same manner as example 1, and then evaluated in the same manner as example 1. The results are shown in Table 3.

Example 10

Ester formed from 3,3'-dithiodipropionic acid and N-hydroxyhexyloctadecyl succinimide (ester (I-10))

To 8.0 g of the N-(6-hydroxyhexyl)octadecyl succinimide obtained in synthesis example 3 were added, under an atmosphere of nitrogen, 1.95 g of 4-dimethylaminopyridine, 1.67 g of 3,3'-dithiodipropionic acid (manufactured by Wako Pure Chemical Industries, Ltd.), 3.06 g of water-soluble carbodiimide hydrochloride and 80 ml of methylene chloride, and the resulting mixture was stirred at room temperature for 4 hours. Following completion of the reaction, the reaction mixture was washed twice with 50 ml samples of a 0.5N aqueous solution of hydrochloric acid, once with 100 ml of a 5% aqueous solution of sodium bicarbonate, and then twice with 100 ml samples of pure water, and the organic layer was then separated. The thus obtained organic layer was dried over anhydrous magnesium sulfate and filtered, and the filtrate was then concentrated using a rotary evaporator. The resulting residue was purified by silica gel column chromatography (mobile phase: ethyl acetate/hexane), and the solvent was then removed to obtain 6.3 g of a white solid (yield: 79%). High performance liquid chromatography was used to confirm that the obtained compound contained no impurities. $^1$H-NMR measurement confirmed that the target compound had been obtained.

$^1$H-NMR (CDCl$_3$, δ ppm): 0.87 (t, 3H), 1.25 (m, 64H), 1.30 (m, 8H), 1.48 (m, 2H), 1.60 (m, 8H), 1.88 (m, 2H), 2.35 (dd, 2H), 2.77 (m, 8H), 2.92 (t, 4H), 3.47 (t, 4H), 4.07 (t, 4H)

With the exception of using the ester (I-10) obtained in the manner described above as the oil additive, sample oils were prepared in the same manner as example 1, and then evaluated in the same manner as example 1. The results are shown in Table 4.

Example 11

Ester formed from 3-thiodipropionic acid and N-hydroxyethyloctadecenyl succinimide (ester (I-11))

To 15.0 g of the N-(2-hydroxyethyl)octadecenyl succinimide obtained in synthesis example 2 were added, under an atmosphere of nitrogen, 5.7 g of 4-dimethylaminopyridine, 3.3 g of 3-thiodipropionic acid (manufactured by Kanto Chemical Co., Inc.), 8.0 g of water-soluble carbodiimide hydrochloride and 50 ml of methylene chloride, and the resulting mixture was stirred at room temperature for 3 hours and then at 35° C. for 1 hour. Following completion of the reaction, the reaction mixture was washed twice with 50 ml samples of a 0.5N aqueous solution of hydrochloric acid, once with 100 ml of a 5% aqueous solution of sodium bicarbonate, and then twice with 100 ml samples of pure water, and the organic layer was then separated. The thus obtained organic layer was dried over anhydrous magnesium sulfate and filtered, and the filtrate was then concentrated using a rotary evaporator. The resulting residue was purified by silica gel column chromatography (mobile phase: ethyl acetate/hexane), and the solvent was then removed to obtain 15.0 g of a white solid (yield: 86%). High performance liquid chromatography was used to confirm that the obtained compound contained no impurities. $^1$H-NMR measurement confirmed that the target compound had been obtained.

$^1$H-NMR (CDCl$_3$, δ ppm): 0.88 (t, 6H), 1.27 (m, 52H), 1.96 (m, 4H), 2.28 (m, 2H), 2.46 (m, 2H), 2.58 (m, 6H), 2.76 (m, 6H), 2.89 (m, 2H), 3.37 (m, 4H), 4.36 (m, 4H), 5.29 (m, 2H), 5.56 (m, 2H)

With the exception of using the ester (I-11) obtained in the manner described above as the oil additive, sample oils were prepared in the same manner as example 1, and then evaluated in the same manner as example 1. However, only the lubricant base oil A was used as the lubricant base oil. The results are shown in Table 4.

Example 12

Ester formed from suberic acid and N-hydroxyethyloctadecyl succinimide (ester (I-12))

A reaction flask was charged with 15.0 g of N-(2-hydroxyethyl)octadecyl succinimide, 3.2 g of suberic acid (manufactured by Tokyo Chemical Industry Co., Ltd.), 5.1 g of 4-dimethylaminopyridine (manufactured by Koei Chemical Co., Ltd.) and 100 ml of methylene chloride (manufactured by Kishida Chemical Co., Ltd.), and following thorough stirring, 8.0 g of 1-ethyl-3-(N,N'-dimethylaminopropyl)carbodiimide (manufactured by Eiweiss Chemical Corporation) was added to the flask at room temperature, and a further 50 ml of methylene chloride was then added. The reaction mixture was stirred at room temperature for 3 hours and then at 35° C. for 3 hours. The reaction mixture was then cooled to room temperature, and washed with 0.5 mol/L hydrochloric acid, a 5% aqueous solution of sodium bicarbonate, and distilled water. The organic layer was then dried over anhydrous magnesium sulfate, the magnesium sulfate was removed by vacuum filtration, and the solvent was then removed from the organic layer by distillation under reduced pressure using a rotary evaporator. The resulting reaction product was purified by silica gel column chromatography (developing solvent: hexane/ethyl acetate), yielding 14.6 g of the target product (yield: 85%).

$^1$H-NMR (CDCl$_3$, δ ppm): 0.88 (t, 6H), 1.28 (m, 68H), 1.49 (m, 2H), 1.60 (m, 4H), 1.90 (m, 2H), 2.35 (t, 4H), 2.39 (m, 2H), 2.81 (m, 4H), 3.75 (m, 4H), 4.22 (m, 4H)

With the exception of using the ester (I-12) obtained in the manner described above as the oil additive, sample oils were prepared in the same manner as example 1, and then evaluated in the same manner as example 1. The results are shown in Table 4. However, only the lubricant A was used as the lubricant base oil.

Examples 13 and 14

Measurement of Coefficient of Friction Following Oxidation Stability Test

Test samples were prepared by dissolving 2 mmol of each of the esters obtained in examples 9 and 11 in 200 ml samples of a poly-α-olefin. And the poly-α-olefin containing no added ester was also prepared, and each sample was heated at 165.5° C. for 96 hours in an internal combustion engine lubricant oxidation stability tester, with the coefficient of friction measured before and after the heating operation using a Soda pendulum-type friction tester (manufactured by Shinko Engineering Co., Ltd.). The coefficient of kinetic friction was calculated from the initial amplitude of the pendulum, the amplitude upon oscillation, and the oscillation frequency. The results are shown in Table 5.

Comparative Example 1

Dioleyl 3,3'-dithiodipropionate (ester (8))

5.0 g of 3,3'-dithiodipropionic acid (manufactured by Wako Pure Chemical Industries, Ltd.), 5.8 g of 4-dimethylaminopyridine (manufactured by Wako Pure Chemical Industries, Ltd.) and 12.8 g of oleyl alcohol (manufactured by Wako Pure Chemical Industries, Ltd.) were stirred and dissolved in 100 mL of methylene chloride (manufactured by Wako Pure Chemical Industries, Ltd.), 10.0 g of 1-ethyl-3-(N,N'-dimethylaminopropyl)carbodiimide (manufactured by Eiweiss Chemical Corporation) was added to the flask, and the reaction mixture was stirred at room temperature and then under heating at 40° C. Following completion of the reaction, the reaction mixture was cooled to room temperature, and washed with 0.5 mol/L hydrochloric acid, distilled water, a saturated aqueous solution of sodium bicarbonate, and a saturated saline solution. The organic layer was then dried over anhydrous magnesium sulfate, and the solvent was removed by distillation at 50° C., yielding 15.1 g of the ester (8) (yield: 89.3%). The physical properties of the ester were as listed below.

$^1$H-NMR (CDCl$_3$, δ ppm): 0.88 (t, 6H), 1.27 (m, 44H), 1.63 (m, 4H), 2.00 (m, 8H), 2.73 (t, 4H), 2.92 (t, 4H), 4.09 (t, 4H), 5.34 (m, 4H)

With the exception of using the ester (8) obtained in the manner described above as the oil additive, sample oils were prepared in the same manner as example 1, and then evaluated in the same manner as example 1. The results are shown in Table 6.

Comparative Example 2

Dioleyl 3,3'-thiodipropionate (ester (9))

5.0 g of 3,3'-thiodipropionic acid (manufactured by Wako Pure Chemical Industries, Ltd.), 6.9 g of 4-dimethylaminopyridine (manufactured by Wako Pure Chemical Industries, Ltd.) and 15.1 g of oleyl alcohol (manufactured by Wako Pure Chemical Industries, Ltd.) were stirred and dissolved in 100 mL of methylene chloride (manufactured by Wako Pure Chemical Industries, Ltd.), 11.8 g of 1-ethyl-3-(N,N'-dimethylaminopropyl)carbodiimide (manufactured by Eiweiss Chemical Corporation) was added to the flask, and the reaction mixture was stirred at room temperature and then under heating at 40° C. Following completion of the reaction, the reaction mixture was cooled to room temperature, and washed sequentially with 0.5 mol/L hydrochloric acid, distilled water, a saturated aqueous solution of sodium bicarbonate, and a saturated saline solution. The organic layer was then dried over anhydrous magnesium sulfate, and the solvent was removed by distillation at 50° C., yielding 17.3 g of the ester (9) (yield: 90.8%). The physical properties of the ester were as listed below.

$^1$H-NMR (CDCl$_3$, δ ppm): 0.88 (t, 6H), 1.27 (m, 44H), 1.62 (m, 4H), 2.02 (m, 8H), 2.60 (t, 4H), 2.80 (t, 4H), 4.09 (t, 4H), 5.34 (m, 4H)

With the exception of using the ester (9) obtained in the manner described above as the oil additive, sample oils were prepared in the same manner as example 1, and then evaluated in the same manner as example 1. The results are shown in Table 6.

Comparative Example 3

Synthesis of Dioleyl Suberate (Ester (10))

5.0 g of suberic acid (manufactured by Wako Pure Chemical Industries, Ltd.), 7.0 g of 4-dimethylaminopyridine (manufactured by Wako Pure Chemical Industries, Ltd.) and 15.4 g of oleyl alcohol (manufactured by Wako Pure Chemical Industries, Ltd.) were stirred and dissolved in 100 mL of methylene chloride (manufactured by Wako Pure Chemical Industries, Ltd.), 12.1 g of 1-ethyl-3-(N,N'-dimethylaminopropyl)carbodiimide (manufactured by Eiweiss Chemical Corporation) was added to the flask, and the reaction mixture was stirred at room temperature and then under heating at 40° C. Following completion of the reaction, the reaction mixture was cooled to room temperature, and washed sequentially with 0.5 mol/L hydrochloric acid, distilled water, a saturated aqueous solution of sodium bicarbonate, and a saturated saline solution. The organic layer was then dried over anhydrous magnesium sulfate, and the solvent was removed by distillation at 50° C., yielding 18.1 g of the ester (10) (yield: 93.2%). The physical properties of the ester were as listed below.

$^1$H-NMR (CDCl$_3$, δ ppm): 0.88 (t, 6H), 1.26 to 1.34 (m, 48H), 1.62 (m, 8H), 2.02 (m, 8H), 2.29 (t, 4H), 4.05 (t, 4H), 5.35 (m, 4H)

With the exception of using the ester (10) obtained in the manner described above as the oil additive, sample oils were prepared in the same manner as example 1, and then evaluated in the same manner as example 1. The results are shown in Table 6.

Comparative Example 4

With the exception of using dibenzyl disulfide (DBDS) manufactured by Tokyo Chemical Industry Co., Ltd. as the oil additive, sample oils were prepared in the same manner as example 1, and then evaluated in the same manner as example 1. The results are shown in Table 7.

TABLE 1

|  | Example 1 | | Example 2 | | Example 3 | |
| --- | --- | --- | --- | --- | --- | --- |
| Additive for oils | Ester (I-1) | | Ester (I-2) | | Ester (I-3) | |
| Lubricant base oil | A | B | A | B | A | B |
| Concentration of additive for oils (mmol/kg) | | | 10 | | | |
| Coefficient of kinetic friction (40° C.) | 0.084 | 0.094 | 0.105 | 0.166 | 0.231 | 0.161 |
| Coefficient of kinetic friction (80° C.) | 0.077 | 0.158 | 0.098 | 0.181 | 0.280 | 0.180 |
| Wear scar diameter (mm) | 0.60 | 0.64 | 0.52 | 0.56 | 0.62 | 0.65 |

TABLE 2

|  | Example 4 | | Example 5 | | Example 6 | |
| --- | --- | --- | --- | --- | --- | --- |
| Additive for oils | Ester (I-4) | | Ester (I-5) | | Ester (I-6) | |
| Lubricant base oil | A | B | B | | A | B |
| Concentration of additive for oils (mmol/kg) | | | 10 | | | |
| Coefficient of kinetic friction (40° C.) | 0.088 | 0.172 | 0.166 | | 0.085 | 0.122 |
| Coefficient of kinetic friction (80° C.) | 0.122 | 0.211 | 0.168 | | 0.084 | 0.164 |
| Wear scar diameter (mm) | 0.60 | 0.61 | 0.52 | | 0.49 | 0.71 |

TABLE 3

|  | Example 7 | | Example 8 | | Example 9 | |
| --- | --- | --- | --- | --- | --- | --- |
| Additive for oils | Ester (I-7) | | Ester (I-8) | | Ester (I-9) | |
| Lubricant base oil | A | B | A | B | A | B |
| Concentration of additive for oils (mmol/kg) | | | 10 | | | |
| Coefficient of kinetic friction (40° C.) | 0.098 | 0.139 | 0.105 | 0.148 | 0.107 | 0.151 |
| Coefficient of kinetic friction (80° C.) | 0.107 | 0.155 | 0.086 | 0.179 | 0.079 | 0.185 |
| Wear scar diameter (mm) | 0.66 | 0.88 | 0.49 | | 0.51 | 0.77 |

TABLE 4

|  | Example 10 | | Example 11 | | Example 12 | |
| --- | --- | --- | --- | --- | --- | --- |
| Additive for oils | Ester (I-10) | | Ester (I-11) | | Ester (I-12) | |
| Lubricant base oil | A | B | A | B | A | B |
| Concentration of additive for oils (mmol/kg) | | | 10 | | | |
| Coefficient of kinetic friction (40° C.) | 0.195 | | 0.106 | | 0.291 | |
| Coefficient of kinetic friction (80° C.) | 0.095 | | 0.085 | | 0.206 | |
| Wear scar diameter (mm) | 0.65 | 0.72 | | | | |

TABLE 5

|  | Example 13 | | Example 14 | |
| --- | --- | --- | --- | --- |
| Additive for oils | Ester (I-9) | | Ester (I-11) | |
| Concentration of additive for oils (mmol/kg) | | | 10 | |
|  | before test | after 96 hours | before test | after 96 hours |
| Coefficient of kinetic friction (40° C.) | 0.107 | 0.097 | 0.106 | 0.096 |
| Coefficient of kinetic friction (80° C.) | 0.079 | 0.083 | 0.085 | 0.081 |

TABLE 6

|  | Comparative example 1 | | Comparative example 2 | | Comparative example 3 | |
| --- | --- | --- | --- | --- | --- | --- |
| Additive for oils | Ester (8) | | Ester (9) | | Ester (10) | |
| Lubricant base oil | A | B | A | B | A | B |
| Concentration of additive for oils (mmol/kg) | | | 10 | | | |
| Coefficient of kinetic friction (40° C.) | 0.312 | 0.156 | 0.427 | 0.177 | 0.275 | 0.198 |
| Coefficient of kinetic friction (80° C.) | 0.379 | 0.183 | 0.457 | 0.206 | 0.246 | 0.213 |
| Wear scar diameter (mm) | 0.70 | 0.93 | 0.74 | 0.84 | 0.66 | 0.74 |

TABLE 7

|  | Comparative example 4 | |
| --- | --- | --- |
| Additive for oils | DBDS | |
| Lubricant base oil | A | B |
| Concentration of additive for oils (mmol/kg) | 10 | |
| Coefficient of kinetic friction (40° C.) | 0.419 | 0.177 |
| Coefficient of kinetic friction (80° C.) | 0.432 | 0.208 |
| Wear scar diameter (mm) | 0.77 | 0.93 |

As is evident from Tables 1 to 4, in each of the examples, a sample oil having excellent friction resistance properties and wear resistance properties was able to be provided regardless of the variety and polarity of the lubricant base oil used. In contrast, as illustrated in Table 6 and Table 7, in the case of the sample oils of comparative examples 1 to 3, the wear resistance properties, in particular, tended to be unsatisfactory, and in the case of the sample oil of comparative example 4, both the friction resistance properties and the wear resistance properties were inferior.

Further, from the results in Table 5 it is clear that the additive for oils of the present invention undergoes minimal variation over time in the coefficient of friction relative to heat history.

INDUSTRIAL APPLICABILITY

The additive for oils containing an ester of the present invention is able to impart favorable wear resistance properties or friction resistance properties to both polar and non-polar oils. Accordingly, the present invention is able to provide an oil such as a lubricant or fuel oil that exhibits favorable wear resistance properties.

Further, because the additive for oils of the present invention undergoes minimal variation over time in the coefficient of friction relative to heat history, it is ideal for addition to automobile transmission oils.

The invention claimed is:

1. An ester compound represented by formula (Ia):

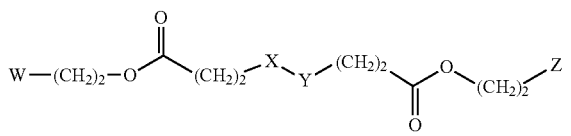

(Ia)

wherein X and Y independently represent a sulfur atom or a single bond; and W and Z are represented by formula (IVa):

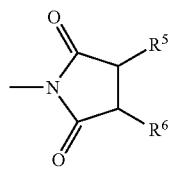

(IVa)

wherein one of $R^5$ and $R^6$ represents an octadecyl or octadecenyl, and the other of $R^5$ and $R^6$ represents a hydrogen atom.

2. A lubricant, comprising an additive for oils and a lubricant base oil, wherein the additive for oils includes an ester represented by formula (I):

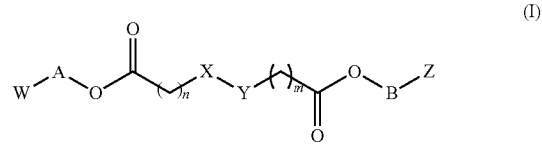

(I)

wherein A and B independently represent a single bond or a hydrocarbylene;

n and m independently represent an integer of 0 to 5, and a sum of n and m represents an integer of 2 to 10;

X and Y independently represent a sulfur atom or a single bond; and

W and Z independently represent a hydrogen atom, a group represented by formula (II):

—NR$^1$R$^2$ (II)

wherein $R^1$ and $R^2$ independently represent a hydrogen atom or an unsubstituted linear alkyl, alkenyl or alkenyl, or $R^1$ and $R^2$ together form a nitrogen-containing heterocyclic group that optionally has one or more substituents in combination with an adjacent nitrogen atom, or a group represented by formula (III):

—N=CR$^3$R$^4$ (III)

wherein $R^3$ and $R^4$ independently represent a hydrogen atom or a hydrocarbyl that optionally has one or more substituents, or $R^3$ and $R^4$ together form a cyclic hydrocarbylidene that optionally has one or more substituents in combination with an adjacent carbon atom, provided that W and Z do not both represent hydrogen atoms.

3. The lubricant according to claim 2, wherein said lubricant base oil is at least one material selected from the group consisting of mineral oils, poly-α-olefins, fatty acid esters, polyalkylene glycols, phosphate esters, silicones, silicate esters, polyphenyl ethers, alkylbenzenes, synthetic naphthenes, gas-to-liquid products, and vegetable oils.

4. The lubricant according to claim 3, wherein said additive is included at 0.001 to 300 mmol per 1 kg of said lubricant.

5. The lubricant according to claim 4, wherein the sum of n and m represents an integer of 4 to 8.

6. The lubricant according to claim 4, wherein said additive is included at 0.01 to 200 mmol per 1 kg of said lubricant.

7. The lubricant according to claim 6, wherein the sum of n and m represents an integer of 4 to 8.

8. The lubricant according to claim 6, wherein said additive is included at 0.1 to 100 mmol per 1 kg of said lubricant.

9. The lubricant according to claim 8, wherein the sum of n and m represents an integer of 4 to 8.

* * * * *